United States Patent
Muraishi et al.

(10) Patent No.: US 8,871,974 B2
(45) Date of Patent: Oct. 28, 2014

(54) IONIC LIQUID CONTAINING PHOSPHONIUM CATION HAVING P—N BOND AND METHOD FOR PRODUCING SAME

(75) Inventors: Kazuki Muraishi, Shibukawa (JP); Kumiko Sueto, Shibukawa (JP); Yuan Gao, Shibukawa (JP)

(73) Assignee: Kanto Denka Kogyo Co., Ltd., Tokyo (JP)

( * ) Notice: Subject to any disclaimer, the term of this patent is extended or adjusted under 35 U.S.C. 154(b) by 506 days.

(21) Appl. No.: 12/094,766

(22) PCT Filed: Nov. 30, 2006

(86) PCT No.: PCT/JP2006/323983
§ 371 (c)(1),
(2), (4) Date: May 22, 2008

(87) PCT Pub. No.: WO2007/063959
PCT Pub. Date: Jun. 7, 2007

(65) Prior Publication Data
US 2009/0163394 A1    Jun. 25, 2009

(30) Foreign Application Priority Data

Dec. 2, 2005  (JP) ................................. 2005-349163
Jul. 10, 2006  (JP) ................................. 2006-188910

(51) Int. Cl.
| | |
|---|---|
| *C07F 9/00* | (2006.01) |
| *C07F 9/6568* | (2006.01) |
| *H01M 6/16* | (2006.01) |
| *H01M 10/0566* | (2010.01) |
| *H01G 9/022* | (2006.01) |
| *H01G 11/62* | (2013.01) |
| *C07F 9/54* | (2006.01) |
| *H01G 9/035* | (2006.01) |
| *H01B 1/12* | (2006.01) |
| *H01M 10/0568* | (2010.01) |
| *H01G 11/56* | (2013.01) |
| *H01G 9/20* | (2006.01) |

(52) U.S. Cl.
CPC ........... *C07F 9/5463* (2013.01); *C07F 9/65688* (2013.01); *H01M 6/162* (2013.01); *H01M 10/0566* (2013.01); *H01G 9/2004* (2013.01); *Y02E 10/542* (2013.01); *H01G 9/038* (2013.01); *H01G 11/62* (2013.01); *Y02E 60/12* (2013.01); *H01M 2300/0025* (2013.01); *H01G 9/035* (2013.01); *C10N 2220/04* (2013.01); *H01B 1/122* (2013.01); *H01M 10/0568* (2013.01); *Y02E 60/13* (2013.01); *H01M 6/166* (2013.01); *H01G 11/56* (2013.01)
USPC .......................................................... 564/14

(58) Field of Classification Search
CPC ............ C07F 9/06; C07F 9/54; C07F 9/5407; C07F 9/5442
USPC .......................................................... 564/14
See application file for complete search history.

(56) References Cited

U.S. PATENT DOCUMENTS

| | | | |
|---|---|---|---|
| 3,755,510 A | 8/1973 | Chan | |
| 3,846,374 A | 11/1974 | Farley et al. | |
| 4,624,755 A | 11/1986 | McManis, III et al. | |
| 5,883,296 A | 3/1999 | Power et al. | |
| 6,103,659 A * | 8/2000 | Pasenok et al. | ............... 502/208 |
| 6,465,643 B1 | 10/2002 | Schiemenz et al. | |
| 6,582,849 B1 | 6/2003 | Heider et al. | |
| 6,794,083 B2 | 9/2004 | Schmidt et al. | |
| 6,893,774 B2 | 5/2005 | Schmidt et al. | |
| 7,297,289 B2 * | 11/2007 | Sato et al. | ..................... 252/62.2 |
| 7,470,829 B2 | 12/2008 | Cadours et al. | |
| 2002/0022182 A1 | 2/2002 | Heider et al. | |
| 2002/0114996 A1 * | 8/2002 | Schmidt et al. | ............... 429/307 |
| 2002/0160261 A1 | 10/2002 | Schmidt et al. | |
| 2002/0193592 A1 * | 12/2002 | Schiemenz et al. | ............. 544/84 |

FOREIGN PATENT DOCUMENTS

| | | |
|---|---|---|
| CA | 2278533 | 7/1998 |
| CA | 2278724 | 8/1998 |
| CA | 2 321 373 | 3/2001 |
| CA | 2361205 | 5/2002 |
| CA | 2491587 | 1/2004 |

(Continued)

OTHER PUBLICATIONS

Schwesinger et al, Chemische Berichte, 1994, 127(12), 2435-54.*
Russian Office Action issued Sep. 15, 2009 in the counterpart application in Russia 2008120238/04(023772).
Office Action from European Patent Office; Application No. 06833786.4-1451; dated Nov. 21, 2013; Applicant Kanto Denka Kogyo Co., Ltd. with Reference No. EP-17923; pp. 1-5.
REAXYS Query No. IDE.XRN=8179583 dated Nov. 15, 2013; Kumar R. Krishna, et al.; 2 pages.
REAXYS Query No. IDE.XRN=5800469 dated Nov. 15, 2013; K. Dimroth, et al.; 11 pages.

(Continued)

*Primary Examiner* — Sudhakar Katakam
(74) *Attorney, Agent, or Firm* — Young & Thompson

(57) ABSTRACT

An ionic liquid which contains an organic matter represented by the following general formula (1) as a cation component. The ionic liquid is stably in a liquid state over a wide temperature range and is excellent in electrochemical stability. The ionic liquid is advantageously used for applications such as electric power storage devices, lithium secondary batteries, electrical double layer capacitors, dye-sensitized solar cells, fuel cells, and reaction solvents.

(1)

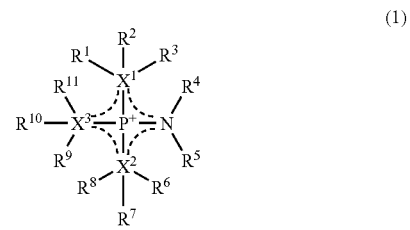

12 Claims, 1 Drawing Sheet

(56) References Cited

FOREIGN PATENT DOCUMENTS

| | | |
|---|---|---|
| CN | 1353134 | 6/2002 |
| EP | 1012796 | 6/1962 |
| EP | 1 070 723 | 1/2001 |
| EP | 1 205 998 | 5/2002 |
| EP | 1 876 181 | 1/2008 |
| GB | 1 012 796 | 12/1965 |
| JP | 2001-508359 | 6/2001 |
| JP | 2001-517205 | 10/2001 |
| JP | 2002-138095 | 5/2002 |
| JP | 2002-513401 | 5/2002 |
| JP | 2002-249670 | 9/2002 |
| JP | 2003-331918 | 11/2003 |
| JP | 2006-36709 | 2/2008 |
| WO | 98/35971 | 8/1998 |
| WO | 02/76924 | 10/2002 |
| WO | 2004/017443 | 2/2004 |
| WO | 2005/006482 | 1/2005 |
| WO | 2005/057772 | 6/2005 |
| WO | 2006/117872 | 11/2006 |
| WO | 2006/118232 | 11/2006 |

OTHER PUBLICATIONS

REAXYS Query No. IDE.XRN=5838431 dated Nov. 15, 2013; E. Nifantyev, et al; 2 pages.
REAXYS Query No. IDE.XRN=7108975 dated Nov. 15, 2013; Makaoto TAKEishi et al. 2 pages.
Francis Carre et al.—"N→P intramolecular stabilization of phosphenium ions and preparation of hypercoordinated phosphanes with unusual properties"—J Organomet. Chem., vol. 529, 1997, pp. 59-68, XP002498438 *compounds 6,7*.
Karl Dimroth et al.—"Reaktionen von Phosphorigsaure-triestern und triamiden mit Carbonium-Ionen"—Chem. Ber.,—vol. 93, 1960, pp. 1649-1658, XP002498439 * Compounds (10), (11)*—*Table p. 1652*.
A.H. Cowley et al.—Reaction of phosphenium ions with 1,3-dienes: a rapid synthesis of phosphorus-containing five-member rings—J. Am. Chem. Soc.,—vol. 105, 1983, pp. 7444-7445, XP002498440—*Compounds 2A-E*.
Hubert Schmidbaur et al.—:Silylated aminophosphonium salts and aminophosphonium methylides—Chemische Berichte , 120(5), 789-94 coden: CHBEAM; ISSN: 0009-2940, 1987, XP002498750—compounds 2B,D.
Koidan, G.N. et al.—"Some properties of triamidophosphazhydrides"—Zhurnal Obshchei Khimii—52(9), Nov. 2001 CODEN: ZOKHA4; ISSN: 0044-460X, 1982, XP008097315—* p. 2006*—*tables 1,6*—CAS RN 83978-39-6.
A. Pleschke et al.—"Halex reactions of aromatic compounds catalysed by 2-azaallenium, carbophosphazenium, aminophosphonium and diphosphazenium salts: a comparative study"—Journal of Fluorine Chemistry (2004) 125(6), 1031-1038 CODEN: JFLCAR; ISSN: * (Et2N)4PBr *.

JP Notice of Rejection dated Mar. 21, 2012, with English Translation, Application No. 2007-548007.
Korean Patent Office issued a Korean Office Action dated Apr. 28, 2010, Application No. 520040401711.
Sisler et al; J. Am. Chem. Soc., vol. 81, 1959, pp. 2983-2985.
European Patent Office Communication—06 833 786.4-1211—Oct. 20, 2010.
Sisler et al., Journal of the American Chemical Society, 1959, vol. 81, p. 2982, 2984; "Reaxys Registry No. 3858757", Database Reaxys [Online] 1959.
Communication dated Dec. 23, 2011 issued from the European Patent Office in European Application No. 06 833 786.4.
M. Mazieres et al., "Reactivite de cations phosphenium R2P+;, vis-a-vis de dienes-1,3 et d'orthoquinones", Bulletin de la Societe Chimique de France, vol. 127, pp. 79-85, 1990.
Canadian Office Action dated Mar. 31, 2011 in corresponding Canadian Application No. 2,630,785.
Chinese Official Action—200680043703.6—Feb. 10, 2011.
Cowley et al.—Reaction of Phosphenium Ions with 1, 3-Dienes: a rapid synthesis of phosphorus-containing five member rings, J. Am. Chem. Soc., vol. 105, pp. 789-794—1983.
A. Pleschke et al.—Halex reactions of aromatic compounds catalysed by 2-azaallenium, carbophosphazenium, aminophosphonium and diphosphazenium salts: a comparative study, Journal of Fluorine Chemistry, vol. 125, pp. 1031-1038, Jun. 20, 2004.
Hubert Schmidbaur et al.—Silylierte Aminophosphonium-Salze und Aminophosphonium-methylide, Chem. Ber, vol. 120, pp. 789-794, Dec. 4, 1986.
Dimroth et al.—Reaktionen von Phosphoriggsaure-triestern und triamiden mit Carbonium-Ionen, Chem. Ber, vol. 93, pp. 1649-1658, 1958.
Carre et al.—N→P intramolecular stabilization of phosphenium ions and preparation of hypercoordinated, phosphanes with unusual properties, Journal of Organometallic Chemistry, vol. 529, pp. 59-68—Jul. 5, 1996.
Rika Hagiwara, Electrochemistry, Electrochemistry, vol. No. 2, pp. 130-136 (2002).
Yasushi Katayama et al., Electrochemical behavior of Silver in 1-Ethyl-3-methylimidazolium Tetrafluoroborate Molten Salt Oct. 29, 2000, pp. C102-C105.
Molten Salt Committee of the Electrochemical Society of Japan, Molten Salts, vol. 44 No. 1 Feb. 2001, 15 pages.
Hajime Matsumoto et al., Highly Conductive Room Temperature Molten Salts Based on Small Trimethylalkylammonium Cations and Bis(trifluoromethysulfonyl)imide, May 20, 2000 , pp. 922-923.
D.R. McFarlane et al., High conductivity molten salts based on the imide ion, Nov. 6, 1998, pp. 1271-1278.
Douglas R. MacFarlane et al., Low viscosity ionic liquids based on organic salts of the dicyanamide anion, Jul. 6, 2001, pp. 1430-1431.

* cited by examiner

[図1]
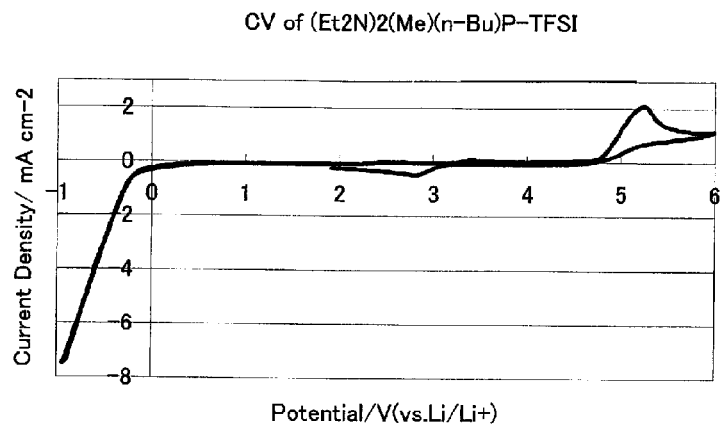
[図2]
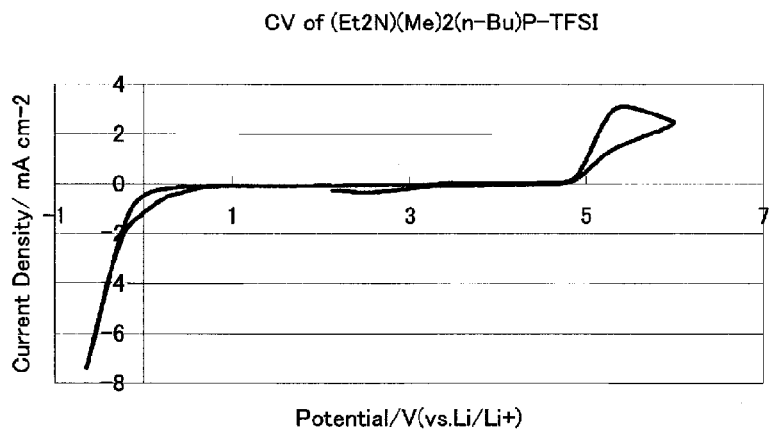
[図3]
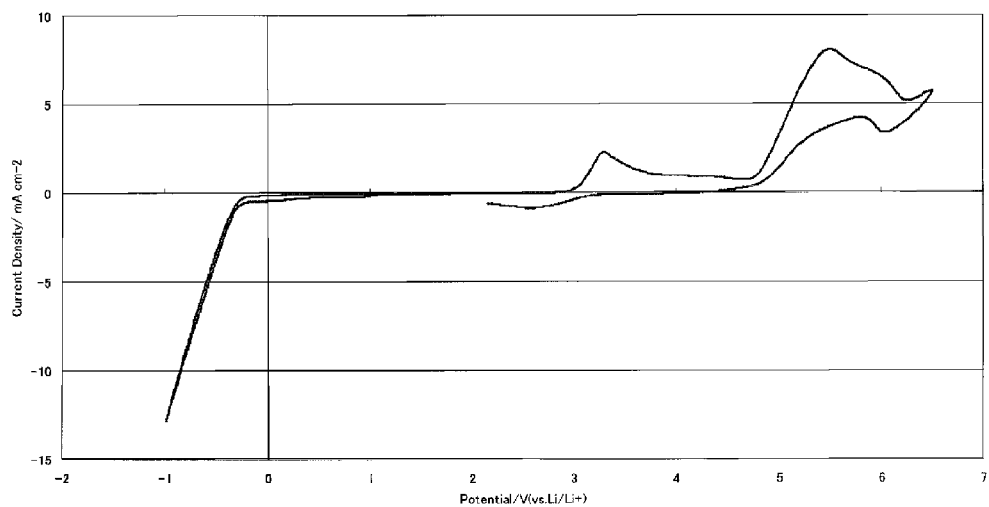

IONIC LIQUID CONTAINING PHOSPHONIUM CATION HAVING P—N BOND AND METHOD FOR PRODUCING SAME

TECHNICAL FIELD

The present invention relates to an ionic liquid that is in a liquid state over a wide temperature range and is excellent in electrochemical stability, to a method for producing the ionic liquid, and to applications thereof including electric power storage devices, lithium secondary batteries, electrical double layer capacitors, dye-sensitized solar cells, fuel cells, reaction solvents, and the like.

BACKGROUND ART

Ionic liquids that have relatively low viscosity and melting point and are represented by an imidazolium system have been reported in many publications so far. However, the ionic liquids reported so far are lacking in stability because they are low in reducing stability and narrow in potential window, and many ionic liquids have disadvantage such as difficulty in applying to an electrolyte for electric power storage devices. Furthermore, among the ionic liquids having relatively low melting point, some ionic liquids are considered to be lacking in stability because they have a low thermal decomposition temperature. (See Patent Document 1 and Non-Patent Documents 1 and 2)

As an ionic liquid stable over a wide temperature range, there has been reported an ionic liquid that is formed using as a cation a nitrogen atom-containing onium represented by an ammonium cation. However, an ionic liquid having an ammonium cation has relatively high melting point and viscosity, and only a few have such a structure that provides a low viscosity liquid at around room temperature. (See Patent Document 2, Patent Document 3, and Non-Patent Documents 3 to 6)

In other words, the fact that there are only a few ionic liquids that are stably in a liquid state over a wide temperature range and excellent in electrochemical stability has posed a large barrier when trying to use an ionic liquid is used for lithium secondary batteries, electrical double layer capacitors, fuel cells, dye-sensitized solar cells, or as an electrolyte, an electrolytic solution, or an additive for electric power storage devices.

Patent Document 1: Japanese Patent Laid-Open Publication No. 2001-517205,
Patent Document 2: International Publication No. WO02/076924,
Patent Document 3: Japanese Patent Laid-Open Publication No. 2003-331918,
Non-Patent Document 1: Hagiwara Rika, Electrochemistry, 70, No. 2, 130 (2002),
Non-Patent Document 2: Y. Katayama, S. Dan, T. Miura and T. Kishi, Journal of The Electrochemical Society, 148 (2), C102-C105 (2001),
Non-Patent Document 3: Matsumoto Hajime and Miyazaki Yoshinori, Yoyuen Oyobi Kouonkagaku, 44, 7 (2001),
Non-Patent Document 4: H. Matsumoto, M. Yanagida, K. Tanimoto, M. Nomura, Y. Kitagawa and Y. Miyazaki, Chem. Lett, 8, 922 (2000),
Non-Patent Document 5: D. R. MacFarlane, J. Sun, J. Golding, P. Meakin and M. Forsyth, Electrochimica Acta, 45, 1271 (2000), and
Non-Patent Document 6: Doulas R. MacFarlane, Jake Golding, Stewart Forsyth, Maria Forsyth and Glen B. Deacon, Chem. Commun., 1430 (2001).

DISCLOSURE OF THE INVENTION

Problems to be Solved by the Invention

It is an object of the present invention to provide an ionic liquid that is stably in a liquid state over a wide temperature range and is excellent in electrochemical stability and a method for producing the ionic liquid, further to provide an ionic liquid that is usable as a material for aforementioned electrolytes, lithium secondary batteries, electrical double layer capacitors, dye-sensitized solar cells, fuel cells, reaction solvents, and the like, particularly to provide an ionic liquid that is stably in a liquid state at around room temperature. Specifically, it is an object of the present invention to provide an ionic liquid that contains a novel phosphonium cation.

Means for Solving the Problems

The present inventors have synthesized a number of salts consisting of a cation component and an anion component, and have made intensive studies on ionic liquids so as to achieve the aforementioned object. As a result, it has been found that an ionic liquid that contains a phosphonium ion having a single or plural P—N bond(s) as a cation component, especially at least one kind selected from the group of organic cations represented by the following general formula (1), is capable of forming an ionic liquid that is stable over a wide temperature range and is excellent in electrochemical stability.

[Chemical formula 1]

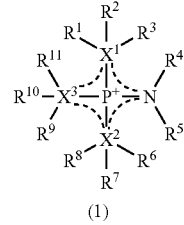

(1)

In the above formula, substituents $R^1$ to $R^{11}$ are independent of each other and may be the same or different from each other. The substituents $R^1$ to $R^{11}$, each represent any of a hydrogen atom, a $C_1$ to $C_{30}$ linear or branched alkyl group, a $C_2$ to $C_{30}$ linear or branched alkenyl group that has a single or plural double bond(s), a $C_2$ to $C_{30}$ linear or branched alkynyl group that has a single or plural triple bond(s), a saturated or partly or fully unsaturated cycloalkyl group, an aryl group, and a heterocyclic group. The hydrogen atom contained in a single or plural substituent(s) $R^1$ to $R^{11}$ may be partly or fully replaced by a halogen atom or partly replaced by a CN group or a $NO_2$ group. Any substituent among the substituents $R^1$ to $R^{11}$ may form a ring structure jointly with each other. The carbon atom contained in the substituents $R^1$ to $R^{11}$ may be replaced by an atom and/or a group of atoms selected from the group consisting of —O—, —Si(R')$_2$—, —C(O)—, —C(O)O—, —S—, —S(O)—, —SO$_2$—, —SO$_3$—, —N=, —N=N—, —NH—, —NR'—, —PR'—, —P(O)R'—, —P(O)R'—O—, —O—P(O)R'—O—, and —P(R')$_2$=N—, wherein R' is a $C_1$ to $C_{10}$ linear or branched alkyl group, an alkyl group that is partly or fully replaced by a fluorine atom, a saturated or partly or fully unsaturated cycloalkyl group, a non-substituted or substituted phenyl group, or a non-substituted or substituted heterocycle. $X^1$, $X^2$, and $X^3$ are independent of each other and represent a nitrogen atom, an oxygen atom, a sulfur atom, or a carbon atom. No two of $X^1$, $X^2$, and $X^3$ are simultaneously a nitrogen atom. $R^3$, $R^8$, or $R^{11}$ is a substituent that exists in the formula only when $X^1$, $X^2$, or $X^3$ is a carbon atom. $X^1$, $R^1$, $R^2$, and $R^3$ may form jointly with each other a saturated or partly or fully unsaturated ring structure when $X^1$ is a carbon atom, $X^2$, $R^6$, $R^7$, and $R^5$ may form jointly with each other a saturated or partly or fully unsaturated ring structure when $X^2$ is a carbon atom, and $X^3$, $R^9$, $R^{10}$, and $R^{11}$ may form jointly with each other a saturated or partly or fully unsaturated ring structure when $X^3$ is a carbon atom. Furthermore, $R^2$, $R^7$, or $R^{10}$ is a substituent that exists in the formula only when $X^1$, $X^2$, or $X^3$ is a nitrogen atom or a carbon atom. $X^1$, $R^1$, and $R^2$ may form jointly with each other a saturated or partly or fully unsaturated ring structure when $X^1$ is a nitrogen atom or a carbon atom, $X^2$, $R^6$, and $R^7$ may form jointly with each other a saturated or partly or fully unsaturated ring structure when $X^2$ is a nitrogen atom or a carbon atom, and $X^3$, $R^9$, and $R^{10}$ may form jointly with each other a saturated or partly or fully unsaturated ring structure when $X^3$ is a nitrogen atom or a carbon atom. Furthermore, dashed lines show a conjugated structure.

In other words, the present invention provides an ionic liquid that contains a phosphonium ion having one, two, or four P—N bonds as a cation component; an ionic liquid that contains an organic substance represented by the general formula (1) as a cation component; and an ionic liquid that is composed of a cation component and an anion component, in which the cation component is a single or plural kind(s) selected from the cation component group represented by the general formula (1), thereby accomplishing the above object.

BRIEF DESCRIPTION OF DRAWINGS

FIG. 1 is a graph showing a CV curve of methylbutyl bis(diethylamino) phosphonium bistrifluoromethane sulfonylimide in Example 2.

FIG. 2 is a graph showing a CV curve of dimethylbutyl (diethylamino) phosphonium bistrifluoromethane sulfonylimide in Example 6.

FIG. 3 is a graph showing a CV curve of tris(diethylamino) di-n-butylaminophosphonium bistrifluoromethane sulfonylimide in Example 13.

BEST MODE FOR CARRYING OUT THE INVENTION

As a cation component represented by the general formula (1), it is preferable that the substituents $R^1$ to $R^{11}$ should be any of a hydrogen atom, a $C_1$ to $C_{30}$ linear or branched alkyl group, a saturated or partly or fully unsaturated cycloalkyl group, an aryl group, and a heterocyclic group and that the hydrogen atom contained in a single or plural substituent(s) $R^1$ to $R^{11}$ should be partly or fully replaced by a halogen atom, or partly replaced by a CN group or a $NO_2$ group. It is also preferable that the carbon atom contained in the substituents $R^1$ to $R^{11}$ should be replaced by an atom and/or a group of atoms selected from the group consisting of —O—, —Si(R')$_2$—, —C(O)—, —C(O)O—, —S—, —S(O)—, and —NR'— (wherein, R' is a $C_1$ to $C_{10}$ linear or branched alkyl group, an alkyl group that is partly or fully replaced by a fluorine atom, a saturated or partly or fully unsaturated cycloalkyl group, a non-substituted or substituted phenyl group, or a non-substituted or substituted heterocycle) To give another example, it is preferable that $R^1$ to $R^{11}$ in the general formula (1), which may be the same or different from each other, each should be a $C_1$ to $C_{20}$ linear or branched alkyl group or alkoxy group.

Examples of the anion component used in the present invention include one or plural kind(s) selected from the group consisting of [RSO$_3$]$^-$, [RfSO$_3$]$^-$, [(RfSO$_2$)$_2$N]$^-$, [(RfSO$_2$)$_3$C]$^-$, [(FSO$_2$)$_3$C]$^-$, [ROSO$_3$]$^-$, [RC(O)O]$^-$, [RfC(O)O]$^-$, [CCl$_3$C(O)O]$^-$, [(CN)$_3$C]$^-$, [(CN)$_2$CR]$^-$, [(RO(O)C)$_2$CR]$^-$, [R$_2$P(O)O]$^-$, [RP(O)O$_2$]$^{2-}$, [(RO)$_2$P(O)O]$^-$, [(RO)P(O)O$_2$]$^{2-}$, [(RO)(R)P(O)O]$^-$, [Rf$_2$P(O)O]$^-$, [RfP(O)O$_2$]$^{2-}$, [B(OR)$_4$]$^-$, [N(CF$_3$)$_2$]$^-$, [N(CN)$_2$]$^-$, [AlCl$_4$]$^-$, PF$_6^-$, [RfPF$_5$]$^-$, [Rf$_3$PF$_3$]$^-$, BF$_4^-$, [RfBF$_3$]$^-$, SO$_4^{2-}$, HSO$_4^-$, NO$_3^-$, F$^-$, Cl$^-$, Br$^-$, and I$^-$, wherein the substituent R is any of a hydrogen atom, a halogen atom, a $C_1$ to $C_{10}$ linear or branched alkyl group, a $C_2$ to $C_{10}$ linear or branched alkenyl group that has a single or plural double bond(s), a $C_2$ to $C_{10}$ linear or branched alkynyl group that has a single or plural triple bond(s), and a saturated or partly or fully unsaturated cycloalkyl group; the hydrogen atom contained in the substituent R may be partly or fully replaced by a halogen atom or partly replaced by a CN group or a NO$_2$ group; the carbon atom contained in the substituent R may be replaced by an atom and/or a group of atoms selected from the group consisting of —O—, —C(O)—, —C(O)O—, —S—, —S(O)—, —SO$_2$—, —SO$_3$—, —N=, —N=N—, —NR'—, —N(R')$_2$—, —PR'—, —P(O)R'—, —P(O)R'—O—, —O—P(O)R'—O—, and —P(R')$_2$=N—, wherein R' is a $C_1$ to $C_{10}$ linear or branched alkyl group, an alkyl group that is partly or fully substituted with a fluorine atom, a saturated or partly or fully unsaturated cycloalkyl group, a non-substituted or substituted phenyl group, or a non-substituted or substituted heterocycle; and Rf is a fluorine-containing substituent. These anion components are combined with the aforementioned cation component and provide an ionic liquid that is stably in a liquid state over a wide temperature range and is excellent in electrochemical stability. Here, "an ionic liquid is stably in a liquid state over a wide temperature range" means that the ionic liquid remains in a liquid state at around 100° C. and has a thermal decomposition temperature that is higher than the melting point thereof by about 200° C. or more, that is considered as a general definition of an ionic liquid at present. In other words, the ionic liquid is stably in a liquid state over this wide temperature range.

These anion components as a counter ion in combination with the cation component represented by the general formula (1) is preferably one or plural kind(s) selected from the group consisting of [RSO$_3$]$^-$, [RfSO$_3$]$^-$, [(RfSO$_2$)$_2$N]$^-$, RfCOO$^-$, PF$_6^-$, BF$_4^-$, [RfBF$_3$]$^-$, [B(OR)$_4$]$^-$, [N(CN)$_2$]$^-$, [AlCl$_4$]$^-$, SO$_4^{2-}$, HSO$_4^-$, NO$_3^-$, F$^-$, Cl$^-$, Br$^-$, and I$^-$, and more preferably one or plural kind(s) selected from the group consisting of [RSO$_3$]$^-$, [RfSO$_3$]$^-$, [(RfSO$_2$)$_2$N]$^-$, RfCOO$^-$, PF$_6^-$, BF$_4^-$, [RfBF$_3$]$^-$, [B(OR)$_4$]$^-$, [N(CN)$_2$]$^-$, [AlCl$_4$]$^-$, SO$_4^{2-}$, HSO$_4^-$, and NO$_3^-$.

A combination of the aforementioned cation components and these preferable anion components provides still more desirable properties, in other words, this provides an ionic liquid that is stably in a liquid state over a wide temperature range from low temperatures and is excellent in electrochemical stability.

A particularly preferable ionic liquid is specified as follows: the anion component used as a counter ion to the cation component represented by the general formula (1) is one or plural kind(s) selected from the group consisting of [RSO$_3$]$^-$, [RfSO$_3$]$^-$, [(RfSO$_2$)$_2$N]$^-$, RfCOO$^-$, PF$_6^-$, BF$_4^-$, [RfBF$_3$]$^-$, [B(OR)$_4$]$^-$, [N(CN)$_2$]$^-$, [AlCl$_4$]$^-$, SO$_4^{2-}$, HSO$_4^-$, NO$_3^-$, F$^-$, Cl$^-$, Br$^-$, and I$^-$; and $R^1$ to $R^{11}$ in the general formula (1)

which may be the same or different from each other, and are each a hydrogen atom or a $C_1$ to $C_{10}$ linear or branched alkyl or alkoxy group.

Furthermore, by lowering the symmetry of the cation represented by the general formula, for example, by carrying out selection in a manner that at least one group among $R^1$ to $R^{11}$ is different from the others, an ionic liquid having a low melting point can be obtained.

In the case where an ionic liquid focused on low melting point is desired, there may be mentioned an ionic liquid that has a cation component specified as follows: at least one of $R^1$ to $R^{11}$ in the general formula (1) is a $C_4$ to $C_{20}$ linear or branched alkyl or alkoxy group and the rest of R″s are a hydrogen atom or a $C_1$ to $C_4$ linear alkyl group, or another ionic liquid that has a cation component specified as follows: at least one of $R^1$ to $R^{11}$ is a silyl group or has a ring structure and the rest of R″s are a hydrogen atom or a $C_1$ to $C_4$ linear alkyl group. A particularly preferable example of combination includes a phosphonium cation that is specified as follows: $X^1$, $X^2$, and $X^3$ are a carbon atom; $R^1$ is a propyl group; $R^2$ and $R^3$ are a hydrogen atom; $R^4$ and $R^5$ are an ethyl group; and $R^6$ to $R^{11}$ are a hydrogen atom, another phosphonium cation that is specified as follows: $X^1$, $X^2$, and $X^3$ are a nitrogen atom; $R^1$ and $R^2$ are a butyl group; and $R^4$, $R^5$, $R^6$, $R^7$, $R^9$, and $R^{10}$ are an ethyl group, another phosphonium cation that is specified as follows: $X^1$, $X^2$, and $X^3$ are a nitrogen atom; $R^1$, $R^2$, $R^4$, $R^6$, and $R^9$ are a methyl group; and $R^5$, $R^7$, and $R^{10}$ are a butyl group, another phosphonium cation that is specified as follows: $X^1$, $X^2$, and $X^3$ are a nitrogen atom; $R^1$ and $R^2$ are an ethyl group; $R^4$, $R^6$, and $R^9$ are a methyl group; and $R^5$, $R^7$, and $R^{10}$ are a butyl group, and the like.

Furthermore, the confirmed effect of lowering the symmetry of the cation on the melting point is exemplified by the following facts. The melting point is about 90° C. of an ionic liquid composed of a cation of which $X^1$, $X^2$, and $X^3$ are a nitrogen atom; and all of $R^1$, $R^2$, $R^4$, $R^5$, $R^6$, $R^7$, $R^9$, and $R^{10}$ are an ethyl group, and an anion of $(CF_3SO_2)_2N^-$. On the other hand, the melting point is about 25° C. of an ionic liquid composed of a cation in which $X^1$, $X^2$, and $X^3$ are a nitrogen atom; $R^1$ and $R^2$ are a butyl group; and all of $R^4$, $R^5$, $R^6$, $R^7$, $R^9$, and $R^{10}$ are an ethyl group, and an anion of $(CF_3SO_2)_2N^-$. Therefore, the melting point is lowered by about 65° C. by lowering the symmetry.

As an anion component that is combined with these cations, there may be mentioned any of $(CF_3SO_2)_2N^-$, $PF_6^-$, and $BF_4^-$, and particularly preferably $(CF_3SO_2)_2N^-$ or $BF_4^-$. An ionic liquid having a low melting point as mentioned above can be used alone as an electrolyte or as a reaction solvent at a low temperature, broadening the applications of ionic liquids.

The above-mentioned ionic liquid of the present invention is stable over a wide temperature range and is excellent in electrochemical stability. Hence, the ionic liquid of the present invention is advantageously used as an electrolyte, an electrolytic solution, an additive, or the like for electric power storage devices, as a material for lithium secondary batteries, electrical double layer capacitors, fuel cells or dye-sensitized solar cells, actuators, or lubricating oil, or as a reaction solvent for various reactions. Furthermore, the ionic liquid of the present invention is also stable against a strong alkali, so that it can be used as a reaction solvent used under alkaline conditions. It has been known that thermal stability is extremely enhanced by using an ionic liquid in place of conventional plasticizers.

Electrolytic deposition of aluminum or aluminum alloys such as Al—Mn, Al—Ti, Al—Mg, and Al—Cr in an ionic liquid has been reported.

By polymerizing an ionic liquid, a polymer material that exhibits unique properties of the ionic liquid containing a high density of ions such as flame retardancy and electrochemical stability can be designed.

Note that, the cation of the general formula (1) is represented as a phosphonium cation having a positive charge localized on the phosphorus atom, but the charge is considered to be delocalized in the molecule.

A typical method for synthesizing an ionic liquid that contains a cation component represented by the general formula (1) is described below.

[Chemical formula 2]

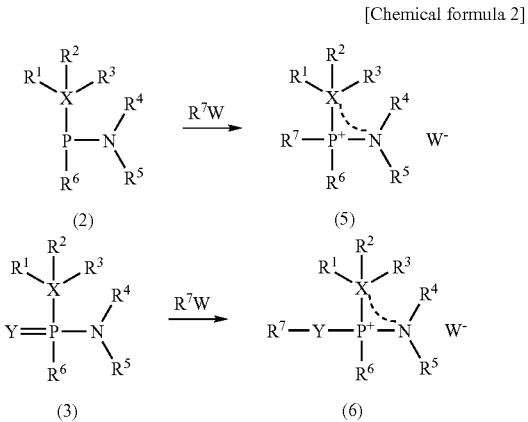

To an organic substance as a raw material represented by the general formula (2) or (3), an alkylation agent ($R^7W$) is added dropwise and resultant mixture is subjected to reaction at a predetermined temperature for a predetermined time. The resulting reaction product is washed with ultrapure water or diethyl ether and the like, and then vacuum-dried. As the alkylation agent ($R^7W$), there are mentioned alkyl iodide, alkyl bromide, alkyl chloride, dialkyl sulfate ester, dialkyl sulfonate ester, dialkyl carbonate ester, trialkyl phosphate alkylmonofluoroalkylsulfonate or alkylpolyfluoroalkylsulfonate, alkylperfluoroalkylsulfonate, alkylmonofluorocarboxylate, or alkylpolyfluorocarboxylate, alkylperfluorocarboxylate, sulfuric acid, nitric acid, hydrochloric acid, and the like.

An ionic liquid containing a cation component that has four P—N bonds and is represented by the general formula (1) is obtained, for example, as follows.

[Chemical formula 3]

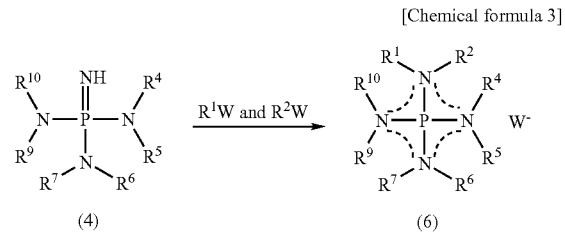

In the above formula, $R^1$ may be the same as $R^2$.

To an organic substance as a raw material represented by the general formula (4), alkylation agents ($R^1W$ and $R^2W$) are added dropwise and the resultant mixture is subjected to reaction at a predetermined temperature for a predetermined time. The resulting reaction product is washed with ultrapure water or diethyl ether and the like, and then vacuum-dried. As the alkylation agents (R¹W and R²W), there are mentioned alkyl iodide, alkyl bromide, alkyl chloride, dialkyl sulfate ester, dialkyl sulfonate ester, dialkyl carbonate ester, trialkyl phosphate ester, alkylmonofluoroalkylsulfonate, or alkylpolyfluoroalkylsulfonate, alkylperfoluoroalkylsulfonate, alkylmonopolyfluorocarboxylate, or alkylpolyfluorocarboxylate, alkylperfluorocarboxylate, sulfuric acid, nitric acid, hydrochloric acid, and the like.

Furthermore, for example, through anion exchange as described below, an ionic liquid having a different anion can also be prepared.

[Chemical formula 4]

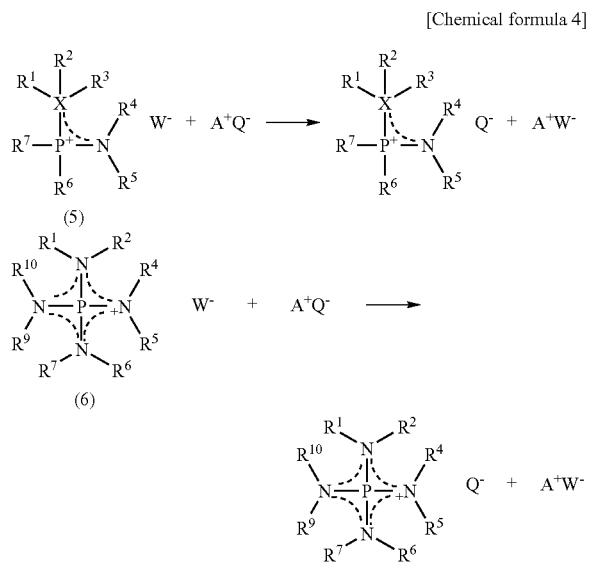

Here, as the ionic compound $A^+Q^-$, there are mentioned, for example, $LiN(CF_3SO_2)_2$, $NaN(CF_3SO_2)_2$, $KN(CF_3SO_2)_2$, $CF_3SO_3Li$, $CF_3SO_3Na$, $CF_3CF_2CF_2CF_2SO_3Li$, $CF_3SO_3K$, $CF_3CH_2SO_3Li$, $CF_3CH_2SO_3Na$, $CF_3CH_2SO_3K$, $CF_3COOLi$, $CF_3COONa$, $CF_3COOK$, $CF_3COOAg$, $CF_3CF_2CF_2COOAg$, $LiPF_6$, $NaPF_6$, $KPF_6$, $LiBF_4$, $NaBF_4$, $KBF_4$, $NH_4BF_4$, $KC_2F_5BF_3$, $LiB(C_2O_4)_2$, $LiSbF_6$, $NaSbF_6$, $KSbF_6$, $NaN(CN)_2$, $AgN(CN)_2$, $Na_2SO_4$, $K_2SO_4$, $NaNO_3$, $KNO_3$, and the like, but the ionic compound is not limited by the above compounds.

The substituents $R^1$ to $R^7$ in the general formula (5) and the substituents $R^1$, $R^2$, $R^4$ to $R^7$, $R^9$, and $R^{10}$ in the general formula (6) may be independently the same or different from each other. These substituents are each any of a hydrogen atom, a halogen atom, a $C_1$ to $C_{30}$ linear or branched alkyl group, a $C_2$ to $C_{30}$ linear or branched alkenyl group that has a single or plural double bond(s), a $C_2$ to $C_{30}$ linear or branched alkynyl group that has a single or plural triple bond(s), a saturated or partly or fully unsaturated cycloalkyl group, an aryl group, and a hetrocyclic group. The hydrogen atom contained in a single or plural substituent(s) may be partly or fully replaced by a halogen atom or partly replaced by a CN group or a $NO_2$ group. Any substituent among the substituents $R^1$ to $R^7$ or any substituent among the substituents $R^1$, $R^2$, $R^4$ to $R^7$, $R^9$, and $R^{10}$ may form a ring structure jointly with each other. The carbon atom contained in these substituents may be replaced by an atom and/or a group of atoms selected from the group consisting of —O—, —Si(R')$_2$—, —C(O)—, —C(O)

O—, —S—, —S(O)—, —SO$_2$—, —SO$_3$—, —N=, —N=N—, —NH—, —NR'—, —PR'—, —P(O)R'—, —P(O)R'—O—, —O—P(O)R'—O—, and —P(R')$_2$=N—, wherein R' is a $C_1$ to $C_{10}$ linear or branched alkyl group, an alkyl group that is partly or fully substituted with a fluorine atom, a saturated or partly or fully unsaturated cycloalkyl group, a non-substituted or substituted phenyl group, or a non-substituted or substituted heterocycle.

As the halogen atom described above, there are mentioned fluorine, chlorine, bromine, and iodine.

As the cycloalkyl group described above, there are mentioned cyclopropyl, cyclobutyl, cyclopentyl, cyclohexyl, cycloheptyl, cyclooctyl, cyclononyl, cylodecyl, and the like. The cycloalkyl group includes a group having an unsaturated bond such as a cycloalkenyl group and a cycloalkynyl group. The cycloalkyl group may be partly or fully substituted with a halogen atom, or may be partly substituted with a CN group or a $NO_2$ group.

As the heterocyclic group described above, there are mentioned pyrodinyl, pyrrolinyl, imidazolidinyl, imidazolinyl, pyrazolidinyl, pyrazonyl, piperidyl, piperadinyl, morpholinyl, thienyl, and the like. These heterocyclic groups may contain one or plural group(s) selected from alkyl, alkoxy, hydroxyl, carboxyl, amino, alkylamino, dialkylamino, thiol, and alkylthio groups, and a halogen atom.

As the aryl group described above, there are mentioned phenyl, cumenyl, mesityl, tolyl, xylyl groups, and the like. These aryl groups may contain one or plural group(s) selected from alkyl, alkoxy, hydroxyl, carboxyl, acyl, formyl, amino, alkylamino, dialkylamino, thiol, and alkylthio groups, and halogen atoms.

In addition, there are mentioned an alkoxyalkyl group such as methoxymethyl, methoxyethyl, ethoxymethyl, and ethoxyethyl, a trialkylsilyl group such as trimethylsilyl group, and the like.

As an anion component Q that is allowed to react and combine with a compound represented by the general formula (4) or (5), there are mentioned the anion components described above.

EXAMPLE

The present invention will be described in detail with reference to the following examples, but these examples should not be construed in any way as limiting the present invention.

Example 1

(a) Preparation of chlorobis(diethylamino)phosphine

In a 300 ml three-necked flask equipped with a dropping funnel and a magnetic stirrer, 10.0 g (0.0728 mol) of phosphorus trichloride and 100 ml of anhydrous diethyl ether were charged at room temperature in a nitrogen gas atmosphere, and the mixture was cooled to 5° C. or less in an ice bath. While the resulting reaction mixture was stirred, 30.0 ml (0.291 mol) of diethylamine were slowly added dropwise to the reaction mixture over 3 hours. The resulting crystals were filtered off under pressure in a nitrogen gas atmosphere. After the crystals were washed with anhydrous diethyl ether three times, they were purified by vacuum-distillation (0.4 kPa, 77.8-78.2° C.), and 8.07 g of chlorobis(diethylamino)phosphine were obtained in the form of a transparent liquid; the yield was 53%.

The resulting compound was identified with a nuclear magnetic resonance analyzer (BRUKER Ultra Shield 300

NMR Spectrometer, manufactured by BRUKER Limited). The resulting spectral data are shown below.

¹H-NMR (300 MHz, solvent: CDCl₃, standard substance: tetramethylsilane)
δ 3.20-3.24 (m, 8H)
1.14 (t, 12H)
³¹P-NMR (121 MHz, solvent: CDCl₃, standard substance: triphenylphosphine)
δ 160.56 (s, 1P)
The structural formula is shown below.

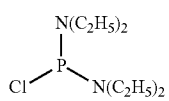

[Chemical formula 5]

(b) Preparation of methylbis(diethylamino)phosphine

In a 200 ml four-necked flask equipped with a refluxing condenser, a dropping funnel, and a magnetic stirrer, 8.07 g (0.038 mol) of chlorobis(diethylamino) phosphine obtained in (a) and 100 ml of anhydrous diethyl ether were charged at room temperature in a nitrogen gas atmosphere, and the mixture was cooled to −78° C. While the reaction mixture was stirred, 38 ml of a diethyl ether solution of 1 mol/L CH₃Li were added dropwise to the reaction mixture. After the reaction mixture was further stirred for 15 minutes, the temperature was elevated slowly, and then the reaction mixture was refluxed for 45 minutes. After the temperature was returned back to room temperature, the resulting crystals were filtered off under pressure in a nitrogen gas atmosphere, and then washed with anhydrous diethyl ether three times. Furthermore, the crystals were purified by vacuum-distillation (0.4 kPa, 63.9-65.7° C.), and 5.10 g of methylbis(diethylamino) phosphine were obtained in the form of a transparent liquid; the yield was 71%.

The resulting compound was identified with a nuclear magnetic resonance analyzer (BRUKER Ultra Shield 300 NMR Spectrometer, manufactured by BRUKER Limited). The resulting spectral data are shown below.

¹H-NMR (300 MHz, solvent: CDCl₃, standard substance: tetramethylsilane)
δ 3.05-2.92 (m, 8H)
1.26 (d, 3H)
1.00 (t, 12H)
³¹P-NMR (121 MHz, solvent: CDCl₃, standard substance: triphenylphosphine)
δ 79.19 (m, 1P)
The structural formula is shown below.

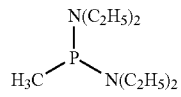

[Chemical formula 6]

(c) Preparation of dimethylbis(diethylamino)phosphonium Methyl Sulfate

In a 50 ml two-necked flask equipped with a magnetic stirrer, 2.82 g (0.0148 mol) of methylbis(diethylamino)phosphine obtained in (b) were charged at room temperature in a nitrogen gas atmosphere, and the mixture was ice-cooled, and then 1.7 ml (0.018 mol) of dimethyl sulfate were added dropwise. After the resulting reaction mixture was stirred at room temperature for 4 hours, it was washed with diethyl ether three times. By vacuum drying at room temperature, 4.25 g of dimethylbis(diethylamino)phosphonium methyl sulfate were obtained in the form of a white solid; the yield was 91%.

The resulting compound was identified with a nuclear magnetic resonance analyzer (BRUKER Ultra Shield 300 NMR Spectrometer, manufactured by BRUKER Limited). The resulting spectral data are shown below.

¹H-NMR (300 MHz, solvent: CDCl₃, standard substance: tetramethylsilane)
δ 3.98 (s, 3H)
3.20-3.08 (m, 8H)
2.14 (d, 6H)
1.19 (t, 12H)
³¹P-NMR (121 MHz, solvent: CDCl₃, standard substance: triphenylphosphine)
δ 62.19 (m, 1P)
The structural formula is shown below (in the formula, the dashed line shows a conjugated structure).

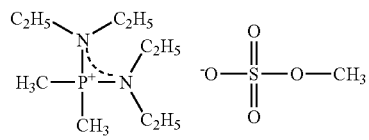

[Chemical formula 7]

(d) Preparation of dimethylbis(diethylamino)phosphonium bistrifluoromethane sulfonylimide In a 100 ml recovery flask equipped with a magnetic stirrer, 4.25 g (0.0134 mol) of dimethylbis(diethylamino)phosphonium methyl sulfate obtained in (c) and 25 ml of ultrapure water were charged. While the resulting reaction mixture was stirred, an aqueous solution dissolving 4.2 g (0.015 mol) of LiTFSI in 25 ml of ultrapure water was added to the reaction mixture, and the resulting mixture was further stirred at room temperature for 15 hours. The resulting salt was extracted with 50 ml of CH₂Cl₂. The water layer was further extracted with 50 ml of CH₂Cl₂. The organic layer was washed with 100 ml of ultrapure water three times, and then the resulting extracted solution was concentrated with a rotary evaporator and vacuum-dried at 80° C. In the form of a white solid, 4.77 g of dimethylbis(diethylamino)phosphonium bistrifluoromethane sulfonylimide were obtained; the yield was 73%.

The resulting compound was identified with a nuclear magnetic resonance analyzer (BRUKER Ultra Shield 300 NMR Spectrometer, manufactured by BRUKER Limited). The resulting spectral data are shown below.

¹H-NMR (300 MHz, solvent: CDCl₃, standard substance: tetramethylsilane)
δ 3.15-3.04 (m, 8H)
1.95 (d, 6H)
1.17 (t, 12H)
¹⁹F-NMR (282 MHz, solvent: CDCl₃, standard substance: CF₃Cl)
δ −78.93 (s, 6F)
³¹P-NMR (121 MHz, solvent: CDCl₃, standard substance: triphenylphosphine)
δ 59.70 (m, 1P)

The structural formula is shown below (in the formula, the dashed line shows a conjugated structure).

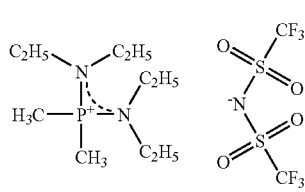

[Chemical formula 8]

The melting point was measured with a differential scanning calorimeter (DSC8230, manufactured by Shimadzu Corp.). The melting point was 38.7° C. and the crystallization temperature was 29.4° C. The thermal decomposition temperature was measured with a thermal gravimetry analyzer (TG8120, manufactured by Rigaku Corp.). The 5% weight-loss temperature measured at a temperature rise rate of 10° C./min was 398.6° C.

Example 2

(e) Preparation of methyl n-butylbis(diethylamino)phosphonium n-butyl sulfate

In a 50 ml two-necked flask equipped with a magnetic stirrer, 2.28 g (0.012 mol) of methylbis(diethylamino)phosphine obtained in (b) were charged at a room temperature in a nitrogen gas atmosphere, and the resultant mixture was ice-cooled, and then 2.85 ml (0.0144 mol) of di-n-butyl sulfate were added dropwise. After the resulting reaction mixture was stirred at room temperature for 21 hours, it was washed with diethyl ether three times and vacuum-dried at room temperature to obtain 3.13 g of methyl n-butylbis(diethylamino)phosphonium n-butyl sulfate in the form of a yellow liquid: the yield was 65%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 4.03 (t, 2H)

3.20-3.08 (m, 8H)

2.47-2.37 (m, 2H)

2.12 (d, 3H)

1.67-1.37 (m, 8H)

1.19 (t, 12H)

0.97 (t, 3H)

0.91 (t, 3H)

$^{31}$P-NMR (121 MHz, solvent: CDCl$_3$, standard substance: triphenylphosphine)

δ 65.23 (m, 1P)

The structural formula is shown below (in the formula, the dashed line shows a conjugated structure).

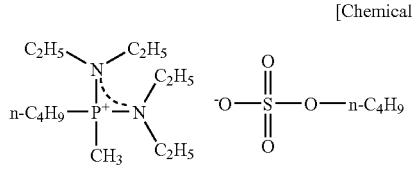

[Chemical formula 9]

(f) Preparation of methyl n-butylbis(diethylamino)phosphonium bistrifluoromethane sulfonylimide In a 100 ml recovery flask equipped with a magnetic stirrer, 3.13 g (0.0078 mol) of methyl n-butylbis(diethylamino)phosphonium n-butyl sulfate obtained in (e) and 25 ml of ultrapure water were charged. While the resulting reaction mixture was stirred, an aqueous solution dissolving 2.5 g (0.0086 mol) of LiTFSI in 25 ml of ultrapure water was added to the reaction mixture, and the resulting mixture was further stirred at room temperature for 15 hours. The resulting salt was extracted with 50 ml of CH$_2$Cl$_2$. The water layer was further extracted with 50 ml of CH$_2$Cl$_2$. The organic layer was washed with 100 ml of ultrapure water three times, and then the resulting extracted solution was concentrated with a rotary evaporator and vacuum-dried at 80° C. In the form of a transparent liquid, 3.02 g of methyl n-butylbis(diethylamino)phosphonium bistrifluoromethane sulfonylimide were obtained; the yield was 73%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.15-3.04 (m, 8H)

2.27-2.18 (m, 2H)

1.91 (d, 3H)

1.55-1.42 (m, 4H)

1.18 (t, 12H)

0.97 (t, 3H)

$^{19}$F-NMR (282 MHz, solvent: CDCl$_3$, standard substance: CF$_3$Cl)

δ -78.86 (s, 6F)

$^{31}$P-NMR (121 MHz, solvent: CDCl$_3$, standard substance: triphenylphosphine)

δ 62.86 (m, 1P)

The structural formula is shown below (in the formula, the dashed line shows a conjugated structure).

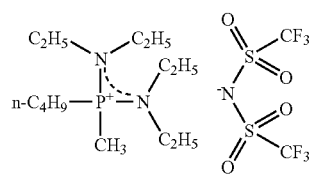

[Chemical formula 10]

The melting point was measured with a differential scanning calorimeter (DSC8230, manufactured by Shimadzu Corp.). The melting point was 15.9° C. and the crystallization temperature was -10.5° C. The thermal decomposition temperature was measured with a thermal gravimetry analyzer (TG8120, manufactured by Rigaku Corp.). The 5% weight-loss temperature measured at a temperature rise rate of 10° C./min was 394.3° C.

The electrical conductivity as measured with the AC impedance method (Electrochemical Measurement System HZ-3000, manufactured by Hokuto Denko Corp.) was 0.088 $Sm^{-1}$ at 25° C.

The potential window was −0.1 V to 4.7 V with respect to $Li/Li^+$, which was obtained from a cyclic voltammogram measured with the Electrochemical Measurement System HZ-3000 manufactured by Hokuto Denko Corp. using Pt for a working electrode and a counter electrode and Li for a reference electrode. A CV curve of methyl n-butylbis(diethylamino)phosphonium bistrifluoromethane sulfonylimide is shown in FIG. 1.

(g) Preparation of methyl n-butylbis(diethylamino)phosphonium tetrafluoroborate

In a 50 ml recovery flask equipped with a magnetic stirrer, 2.00 g (0.0050 mol) of methyl n-butylbis(diethylamino)phosphonium n-butyl sulfate obtained in (e) and 10 ml of ultrapure water were charged. While the resulting reaction mixture was stirred, an aqueous solution dissolving 0.6 g (0.0055 mol) of $NH_4BF_4$ in 10 ml of ultrapure water was added to the reaction mixture, and the resulting mixture was further stirred at room temperature for 15 hours. The resulting salt was extracted with 20 ml of $CH_2Cl_2$, and the water layer was further extracted with 20 ml of $CH_2Cl_2$. The organic layer was washed with 50 ml of ultrapure water three times, and then the resulting extracted solution was concentrated with a rotary evaporator and vacuum-dried at 80° C. In the form of a white solid, 0.93 g of methyl n-butylbis(diethylamino)phosphonium tetrafluoroborate was obtained; the yield was 53%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.12 (m, 8H)

2.28 (m, 2H)

1.97 (d, 3H)

1.57-1.46 (m, 4H)

1.18 (t, 12H)

0.97 (t, 3H)

$^{19}$F-NMR (282 MHz, solvent: $CDCl_3$, standard substance: $CF_3Cl$)

δ −152.51 (d, 4F)

$^{31}$P-NMR (121 MHz, solvent: $CDCl_3$, standard substance: triphenylphosphine)

δ 63.80 (m, 1P)

The structural formula is shown below (in the formula, the dashed line shows a conjugated structure).

[Chemical formula 11]

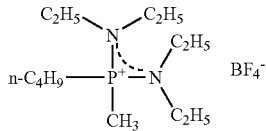

The melting point was measured with a differential scanning calorimeter (DSC8230, manufactured by Shimadzu Corp.). The melting point was 16.9° C. and the crystallization temperature was −19.9° C. The thermal decomposition temperature was measured with a thermal gravimetry analyzer (TG8120, manufactured by Rigaku Corp.). The 5% weight-loss temperature measured at a temperature rise rate of 10° C./min was 363.0° C.

(h) Preparation of methyl n-butylbis(diethylamino)phosphonium hexafluorophosphate In a 50 ml recovery flask equipped with a magnetic stirrer, 2.00 g (0.0050 mol) of methyl n-butylbis(diethylamino)phosphonium n-butyl sulfate obtained in (e) and 10 ml of ultrapure water were charged. While the resulting reaction mixture was stirred, an aqueous solution dissolving 0.84 g (0.0055 mol) of $LiPF_6$ in 10 ml of ultrapure water was added to the reaction mixture, and the resulting mixture was further stirred at room temperature for 15 hours. The resulting salt was extracted with 20 ml of $CH_2Cl_2$, and the water layer was further extracted with 20 ml of $CH_2Cl_2$. The organic layer was washed with 50 ml of ultrapure water three times, and then the resulting extracted solution was concentrated with a rotary evaporator and vacuum-dried at 80° C. In the form of a white solid, 1.78 g of methyl n-butylbis(diethylamino) phosphonium hexafluorophosphate was obtained; the yield was 83%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.11 (m, 8H)

2.23 (m, 2H)

1.92 (d, 3H)

1.58-1.43 (m, 4H)

1.18 (t, 12H)

0.97 (t, 3H)

$^{19}$F-NMR (282 MHz, solvent: $CDCl_3$, standard substance: $CF_3Cl$)

δ −72.75 (d, 6F)

$^{31}$P-NMR (121 MHz, solvent: $CDCl_3$, standard substance: triphenylphosphine)

δ 63.80 (m, 1P)

−144.29 (hept, 1P)

The structural formula is shown below (in the formula, the dashed line shows a conjugated structure).

[Chemical formula 12]

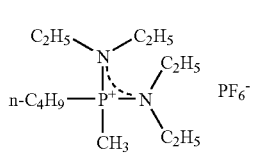

The melting point was measured with a differential scanning calorimeter (DSC8230, manufactured by Shimadzu Corp.). The melting point was 140.0° C. The thermal decomposition temperature was measured with a thermal gravimetry analyzer (TG8120, manufactured by Rigaku Corp.). The 5% weight-loss temperature measured at a temperature rise rate of 10° C./min was 373.0° C.

Example 3

(i) Preparation of bis(diethylamino)(trimethylsilylmethyl)phosphine

In a 50 ml three-necked flask equipped with a dropping funnel and a magnetic stirrer, 0.36 g (14.8 mmol) of magnesium and 10 ml of anhydrous diethyl ether were charged at room temperature in a nitrogen gas atmosphere. After several drops of 1,2-dibromoethane were added so as to activate magnesium, 2.0 ml (14.2 mmol) of chloromethyltrimethylsilane were added dropwise carefully to avoid heat build-up. When the reaction solution was stirred for 1 hour while it was heated mildly with a drier, the solution darkened. Then, after the solution was cooled to −78° C., 3.0 g (14.2 mmol) of chlorobis(diethylamino)phosphine synthesized in (a) were added dropwise to the solution, and the resultant mixture was then returned to room temperature and refluxed for 1 hour. The resulting crystals were filtered off, washed with anhydrous diethyl ether, and purified by vacuum-distillation (0.2 kPa, 74.3-79.5° C.) to obtain 2.29 g of bis(diethylamino)(trimethylsilylmethyl)phosphine in the form of a colorless transparent liquid; the yield was 62%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 2.98-2.84 (m, 8H)

0.95 (m, 14H)

0.00 (s, 9H)

$^{31}$P-NMR (121 MHz, solvent: CDCl$_3$, standard substance: triphenylphosphine)

δ 84.01 (s, 1P)

The structural formula is shown below.

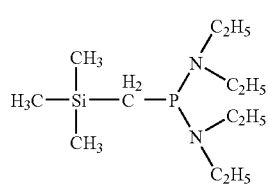

[Chemical formula 13]

(j) Preparation of bis(diethylamino)(methyl)(trimethylsilylmethyl)phosphonium methyl sulfate In a 50 ml two-necked flask equipped with a magnetic stirrer, 1.15 g (0.0044 mol) of bis(diethylamino)(trimethylsilylmethyl) phosphine obtained in (i) were charged at room temperature in a nitrogen gas atmosphere, ice-cooled, and then 0.50 ml (0.0053 mol) of dimethyl sulfate was added dropwise. After the resulting reaction mixture was stirred at room temperature for 18 hours, it was washed with diethyl ether three times. The reaction mixture was vacuum-dried at room temperature, and 1.34 g of bis(diethylamino)(methyl)(trimethylsilylmethyl)phosphonium methyl sulfate was obtained in the form of a white solid; the yield was 79%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.49 (s, 3H)

3.33-3.20 (m, 8H)

2.27-2.16 (m, 5H)

1.21 (t, 9H)

0.30 (s, 9H)

$^{31}$P-NMR (121 MHz, solvent: CDCl$_3$, standard substance: triphenylphosphine)

δ 62.07 (m, 1P)

The structural formula is shown below (in the formula, the dashed line shows a conjugated structure).

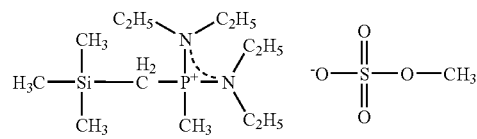

[Chemical formula 14]

(k) Preparation of bis(diethylamino)(methyl)(trimethylsilylmethyl)phosphonium bistrifluoromethane sulfonylimide In a 50 ml recovery flask equipped with a magnetic stirrer, 1.34 g (0.0035 mol) of bis(diethylamino)(methyl)(trimethylsilylmethyl)phosphonium methyl sulfate obtained in (j) and 10 ml of ultrapure water were charged. While the resulting reaction mixture was stirred, an aqueous solution dissolving 1.1 g (0.0038 mol) of LiTFSI in 10 ml of ultrapure water was added to the reaction mixture, and the resulting mixture was further stirred at room temperature for 15 hours. The resulting salt was extracted with 20 ml of CH$_2$Cl$_2$, and the water layer was further extracted with 20 ml of CH$_2$Cl$_2$. The organic layer was washed with 20 ml of ultrapure water three times, and then the resulting extracted solution was concentrated with a rotary evaporator and vacuum-dried at 80° C. In the form of a transparent liquid, 1.13 g of bis(diethylamino)(methyl)(trimethylsilylmethyl) phosphonium bistrifluoromethane sulfonylimide were obtained; the yield was 58%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.09 (m, 8H)

1.94 (d, 3H)

1.70 (d, 2H)

1.17 (t, 9H)

0.25 (s, 9H)

$^{19}$F-NMR (282 MHz, solvent: CDCl$_3$, standard substance: CF$_3$Cl)

δ −78.78 (s, 6F)

$^{31}$P-NMR (121 MHz, solvent: CDCl$_3$, standard substance: triphenylphosphine)

δ 60.62 (m, 1P)

The structural formula is shown below (in the formula, the dashed line shows a conjugated structure).

[Chemical formula 15]

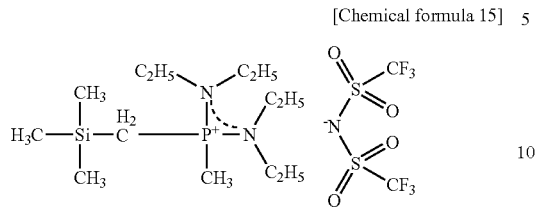

The melting point was measured with a differential scanning calorimeter (DSC8230, manufactured by Shimadzu Corp.). The melting point was 32.1° C. The crystallization temperature was 12.2° C. The glass transition temperature was −65.8° C. The thermal decomposition temperature was measured with a thermal gravimetry analyzer (TG8120, manufactured by Rigaku Corp.). The 5% weight-loss temperature measured at a temperature rise rate of 10° C./min was 229.8° C.

Example 4

(l) Preparation of 1,1-bis(diethylamino)-3-methyl-3-phospholenium bistrifluoromethane sulfonylimide In a 200 ml three-necked flask equipped with a dropping funnel and a magnetic stirrer, 1.90 g (0.0142 mol) of aluminum chloride and 30 ml of anhydrous dichloromethane were charged at room temperature in a nitrogen gas atmosphere. While ice cooling, a solution dissolving 3.0 g (0.0142 mol) of chlorobis(diethylamino) phosphine synthesized in (a) in 25 ml of anhydrous dichloromethane was added dropwise. After the resulting reaction mixture was stirred for 1 hour and cooled to 0° C., 1.42 ml (0.0142 mol) of isoprene was added dropwise. The reaction mixture was stirred at room temperature for 1 hour. Subsequently, 4.5 g (0.016 mol) of LiTFSI were added to the reaction mixture, and the resulting mixture was then stirred overnight at room temperature. Then, the reaction mixture was washed with ultrapure water until the turbidity was not recognized. The resulting organic layer was concentrated with a rotary evaporator, washed with diethyl ether three times, vacuum-dried at 80° C., and 0.94 g of 1,1-bis(diethylamino)-3-methyl-3-phospholenium bistrifluoromethane sulfonylimide was obtained in the form of white crystals; the yield was 13%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)
δ 5.69 (d, 1H)
3.15 (m, 8H)
3.00-2.91 (m, 4H)
1.92 (s, 3H)
1.19 (t, 9H)
$^{19}$F-NMR (282 MHz, solvent: CDCl$_3$, standard substance: CF$_3$Cl)
δ −78.87 (s, 6F)
$^{31}$P-NMR (121 MHz, solvent: CDCl$_3$, standard substance: triphenylphosphine)
δ 81.46 (m, 1P)

The structural formula is shown below (in the formula, the dashed line shows a conjugated structure).

[Chemical formula 16]

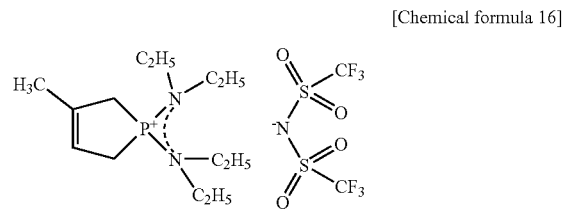

The melting point was measured with a differential scanning calorimeter (DSC8230, manufactured by Shimadzu Corp.). The melting point was 33.3° C. The crystallization temperature was 22.1° C. The thermal decomposition temperature was measured with a thermal gravimetry analyzer (TG8120, manufactured by Rigaku Corp.). The 5% weight-loss temperature measured at a temperature rise rate of 10° C./min was 346.1° C.

Example 5

(m) Preparation of chloro(N,N'-dimethylethylenediamino)phosphine

In a 1000 ml three-necked flask equipped with a dropping funnel and a magnetic stirrer, 31.9 g (0.233 mol) of phosphorus trichloride and 500 ml of anhydrous diethyl ether were charged at room temperature in a nitrogen gas atmosphere, and the mixture was cooled to 5° C. or less in an ice bath. While the resulting reaction mixture was stirred, 25.0 ml (0.233 mol) of N,N'-dimethylethylenediamine were slowly added dropwise to the reaction mixture. Furthermore, 65.0 ml (0.465 mol) of triethylamine were slowly added dropwise. After the reaction mixture was further stirred for 1.5 hours, it was filtered under pressure in a nitrogen gas atmosphere. After the resulting crystals were washed with anhydrous diethyl ether three times, they were purified by vacuum-distillation (0.4 kPa, 44-52° C.), and 16.28 g of chloro(N,N'-dimethylethylenediamino)phosphine were obtained in the form of a transparent liquid; the yield was 46%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)
δ 3.32 (d, 4H)
2.78 (d, 6H)
$^{31}$P-NMR (121 MHz, solvent: CDCl$_3$, standard substance: triphenylphosphine)
δ 171.30 (s, 1P)

The structural formula is shown below.

[Chemical formula 17]

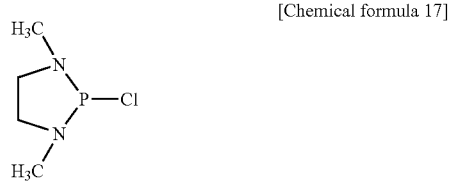

(n) Preparation of methyl(N,N'-dimethylethylenediamino)phosphine

In a 200 ml four-necked flask equipped with a refluxing condenser, a dropping funnel, and a magnetic stirrer, 8.00 g (0.0524 mol) of chloro(N,N'-dimethylethylenediamino)phosphine obtained in (m) and 100 ml of anhydrous diethyl ether were charged at room temperature in a nitrogen gas atmosphere, and the mixture was cooled to −78° C. While the resulting reaction mixture was stirred, 53 ml of a diethyl ether solution of 1 mol/L CH$_3$Li were added dropwise to the reaction mixture. While the reaction mixture was further stirred, the temperature was elevated slowly, and then the reaction mixture was refluxed for 1 hour. After the temperature was returned back to room temperature, the resulting crystals were filtered off under pressure in a nitrogen gas atmosphere, and then washed with anhydrous diethyl ether three times. The crystals were purified by vacuum distillation (4.6 kPa, 62.3° C.), and 3.76 g of methyl(N,N'-dimethylethylenediamino)phosphine were obtained in the form of a transparent liquid; the yield was 54%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.21-3.16 (m, 2H)

3.01-2.96 (m, 2H)

2.64 (d, 6H)

0.89 (d, 3H)

$^{31}$P-NMR (121 MHz, solvent: CDCl$_3$, standard substance: triphenylphosphine)

δ 118.38 (s, 1P)

The structural formula is shown below.

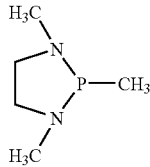

[Chemical formula 18]

(o) Preparation of Methyl n-butyl(N,N'-dimethylethylenediamino)phosphonium iodide In a 50 ml two-necked flask equipped with a magnetic stirrer, 0.80 g (0.0061 mol) of methyl(N,N'-dimethylethylenediamino)phosphine obtained in (n) was charged at room temperature in a nitrogen gas atmosphere and ice-cooled, and then 1.15 g (0.0062 mol) of n-butyl iodide were added dropwise. After the resulting reaction mixture was stirred at room temperature for 16 hours, it was washed with diethyl ether three times. By vacuum drying at room temperature, 1.65 g of methyl n-butyl(N,N'-dimethylethylenediamino)phosphonium iodide were obtained in the form of a white solid; the yield was 86%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: D$_2$O, standard substance: 2,2-dimethyl-2-silapentane-5-sulfonate)

δ 3.28 (d-d, 4H)

2.68 (d, 6H)

2.24 (m, 2H)

1.75 (d, 3H)

1.39-1.30 (m, 4H)

0.81 (t, 3H)

$^{31}$P-NMR (121 MHz, solvent: D$_2$O, standard substance: triphenylphosphine)

δ 80.69 (m, 1P)

The structural formula is shown below (in the formula, the dashed line shows a conjugated structure).

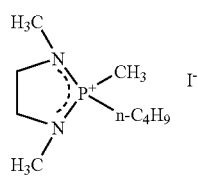

[Chemical formula 19]

(p) Preparation of Methyl n-butyl(N,N'-dimethylethylenediamino)phosphonium bistrifluoromethane sulfonylimide In a 50 ml recovery flask equipped with a magnetic stirrer, 1.65 g (0.0052 mol) of methyl n-butyl(N,N'-dimethylethylenediamino)phosphonium iodide obtained in (O) and 10 ml of ultrapure water were charged. While the resulting reaction mixture was stirred, an aqueous solution dissolving 1.7 g (0.0057 mol) of LiTFSI in 10 ml of ultrapure water was added to the reaction mixture, and the resulting mixture was further stirred at room temperature for 15 hours. The resulting salt was extracted with 20 ml of CH$_2$Cl$_2$, and the water layer was further extracted with 20 ml of CH$_2$Cl$_2$. The organic layer was washed with 20 ml of ultrapure water three times, and then the resulting extracted solution was concentrated with a rotary evaporator and vacuum-dried at 80° C. In the form of a transparent liquid, 0.31 g of methyl n-butyl(N,N'-dimethylethylenediamino)phosphonium bistrifluoromethane sulfonylimide was obtained; the yield was 13%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.38 (d-d, 4H)

2.80 (d, 6H)

2.27 (m, 2H)

1.84 (d, 3H)

1.47-1.36 (m, 4H)

0.93 (t, 3H)

$^{19}$F-NMR (282 MHz, solvent: CDCl$_3$, standard substance: CF$_3$Cl)

δ −78.95 (s, 6F)

$^{31}$P-NMR (121 MHz, solvent: CDCl$_3$, standard substance: triphenylphosphine)

δ 80.66 (m, 1P)

The structural formula is shown below (in the formula, the dashed line shows a conjugated structure).

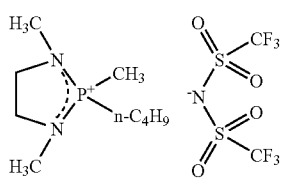

[Chemical formula 20]

The melting point was measured with a differential scanning calorimeter (DSC8230, manufactured by Shimadzu Corp.). The melting point was 30.7° C. The crystallization temperature was 5.9° C. The thermal decomposition temperature was measured with a thermal gravimetry analyzer (TG8120, manufactured by Rigaku Corp.). The 5% weight-loss temperature measured at a temperature rise rate of 10° C./min was 337.2° C.

Example 6

(q) Preparation of dichloro(diethylamino)phosphine

In a 300 ml three-necked flask equipped with a dropping funnel and a magnetic stirrer, 6.0 ml (0.069 mol) of phosphorus trichloride and 100 ml of anhydrous diethyl ether were charged at room temperature in a nitrogen gas atmosphere, and the mixture was cooled to 5° C. or less in an ice bath. While the resulting reaction mixture was stirred, 7.1 ml (0.069 mol) of diethylamine were slowly added dropwise over 3 hours. The reaction mixture was filtered under pressure in a nitrogen gas atmosphere. The resulting crystals were washed with anhydrous diethyl ether three times and purified by vacuum-distillation (0.4 kPa, 27.3-28.2° C.), and 6.84 g of dichloro(diethylamino)phosphine were obtained in the form of a transparent liquid; the yield was 57%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.40-3.29 (m, 4H)

1.19 (t, 8H)

$^{31}$P-NMR (121 MHz, solvent: CDCl$_3$, standard substance: triphenylphosphine)

δ 162.67 (s, 1P)

The structural formula is shown below.

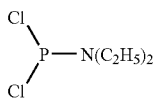

[Chemical formula 21]

(r) Preparation of dimethyl(diethylamino)phosphine

In a 200 ml four-necked flask equipped with a refluxing condenser, a dropping funnel, and a magnetic stirrer, 5.23 g (0.0312 mol) of dichloro(diethylamino) phosphine obtained in (q) and 60 ml of anhydrous diethyl ether were charged at room temperature in a nitrogen gas atmosphere, and the mixture was cooled to −78° C. While the resulting reaction mixture was stirred, 60 ml of a diethyl ether solution of 1 mol/L CH$_3$Li were added dropwise to the reaction mixture. After the reaction mixture was further stirred for 15 minutes, the temperature was elevated slowly, and then the reaction mixture was refluxed for 45 minutes. After the temperature was returned back to room temperature, the resulting crystals were filtered off under pressure in a nitrogen gas atmosphere, and then washed with anhydrous diethyl ether three times. The crystals were purified by vacuum-distillation (10.8 kPa, 69.5-70.0° C.), and 1.87 g of dimethyl(diethylamino)phosphine were obtained in the form of a transparent liquid; the yield was 45%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 2.97-2.86 (m, 4H)

1.09 (d, 6H)

1.01 (t, 6H)

$^{31}$P-NMR (121 MHz, solvent: CDCl$_3$, standard substance: triphenylphosphine)

δ 35.04 (m, 1P)

The structural formula is shown below.

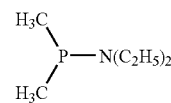

[Chemical formula 22]

(s) Preparation of dimethyl n-butyl(diethylamino)phosphonium n-butyl sulfate

In a 50 ml two-necked flask equipped with a magnetic stirrer, 0.62 g (0.0046 mol) of dimethyl(diethylamino)phosphine obtained in (r) was charged at room temperature in a nitrogen gas atmosphere, ice-cooled, and then 1.1 ml (0.0056 mol) of di-n-butyl sulfate were added dropwise. After the reaction mixture was stirred at room temperature for 42 hours, it was washed with diethyl ether three times. By vacuum drying at room temperature, 1.18 g of dimethyl n-butyl(diethylamino)phosphonium n-butyl sulfate were obtained in the form of a white solid; the yield was 75%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: acetone-d$_6$, standard substance: tetramethylsilane)

δ 3.85 (t, 2H)

3.27 (m, 4H)

2.53 (m, 2H)

2.16 (d, 6H)

1.62-1.39 (m, 8H)

1.19 (t, 6H)

0.98-0.88 (m, 6H)

$^{31}$P-NMR (121 MHz, solvent: acetone-d$_6$, standard substance: triphenylphosphine)

δ 61.67 (m, 1P)

The structural formula is shown below.

[Chemical formula 23]

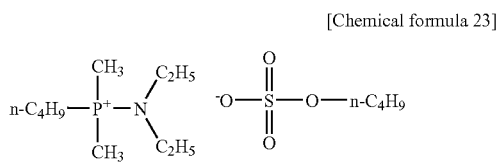

(t) Preparation of dimethyl n-butyl(diethylamino)phosphonium bistrifluoromethane sulfonylimide In a 100 ml recovery flask equipped with a magnetic stirrer, 1.15 g (0.0034 mol) of dimethyl n-butyl(diethylamino) phosphonium n-butyl sulfate obtained in (s) and 25 ml of ultrapure water were charged. While the resulting reaction mixture was stirred, an aqueous solution dissolving 1.2 g (0.0042 mol) of LiTFSI in 25 ml of ultrapure water was added to the reaction mixture, and the resulting mixture was further stirred at room temperature for 14 hours. The resulting salt was extracted with 50 ml of $CH_2Cl_2$, and the water layer was further extracted with 50 ml of $CH_2Cl_2$. After the resulting organic layer was washed with 100 ml of ultrapure water three times, the extracted solution was concentrated with a rotary evaporator, and vacuum-dried at 80° C. In the form of a transparent liquid, 1.39 g of dimethyl n-butyl(diethylamino)phosphonium bistrifluoromethane sulfonylimide were obtained; the yield was 87%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.10 (m, 4H)
2.19 (m, 2H)
1.91 (d, 6H)
1.48 (m, 4H)
1.17 (t, 6H)
0.95 (t, 3H)
$^{19}$F-NMR (282 MHz, solvent: $CDCl_3$, standard substance: $CF_3Cl$)
δ −78.93 (s, 6F)
$^{31}$P-NMR (121 MHz, solvent: $CDCl_3$, standard substance: triphenylphosphine)
δ 59.45 (m, 1P)

The structural formula is shown below.

[Chemical formula 24]

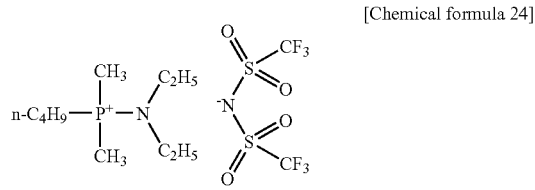

The melting point was measured with a differential scanning calorimeter (DSC8230, manufactured by Shimadzu Corp.). The melting point was −11° C. The crystallization temperature was −19.1° C. The glass transition temperature was −77.3° C. The thermal decomposition temperature was measured with a thermal gravimetry analyzer (TG8120, manufactured by Rigaku Corp.). The 5% weight-loss temperature measured at a temperature rise rate of 10° C./min was 284.0° C.

The electrical conductivity as measured with the AC impedance method (Electrochemical Measurement System HZ-3000, manufactured by Hokuto Denko Corp.) was 0.123 $Sm^{-1}$ at 25° C.

The potential window was 0 V to 4.7 V with respect to $Li/Li^+$, which was obtained from a cyclic voltammogram measured with the Electrochemical Measurement System HZ-3000 manufactured by Hokuto Denko Corp. using Pt for a working electrode and a counter electrode and Li for a reference electrode. A CV curve of dimethyl n-butyl(diethylamino)phosphonium bistrifluoromethane sulfonylimide is shown in FIG. 2.

(u) Preparation of Dimethyl n-butyl(diethylamino)phosphonium hexafluorophosphate In a 50 ml recovery flask equipped with a magnetic stirrer, 1.00 g (0.0029 mol) of dimethyl n-butyl(diethylamino) phosphonium n-butyl sulfate obtained in (s) and 10 ml of ultrapure water were charged. While the resulting reaction mixture was stirred, an aqueous solution dissolving 0.49 g (0.0032 mol) of $LiPF_6$ in 10 ml of ultrapure water was added to the reaction mixture, and the resulting mixture was further stirred at room temperature for 14 hours. The resulting salt was extracted with 20 ml of $CH_2Cl_2$. The water layer was further extracted with 20 ml of $CH_2Cl_2$. The organic layer was washed with 50 ml of ultrapure water three times, and then the resulting extracted solution was concentrated with a rotary evaporator and vacuum-dried at 80° C. In the form of a transparent liquid, 0.62 g of dimethyl n-butyl(diethylamino)phosphonium hexafluorophosphate was obtained; the yield was 46%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.10 (m, 4H)
2.19 (m, 2H)
1.91 (d, 6H)
1.48 (m, 4H)
1.17 (t, 6H)
0.95 (t, 3H)
$^{19}$F-NMR (282 MHz, solvent: $CDCl_3$, standard substance: $CF_3Cl$)
δ −71.70 (d, 6F)
$^{31}$P-NMR (121 MHz, solvent: $CDCl_3$, standard substance: triphenylphosphine)
δ 59.94 (m, 1P)
−144.24 (hept, 1P)

The structural formula is shown below.

[Chemical formula 25]

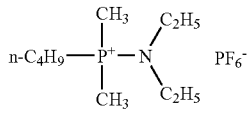

The melting point was measured with a differential scanning calorimeter (DSC8230, manufactured by Shimadzu Corp.). The melting point was 138.1° C. The thermal decomposition temperature was measured with a thermal gravimetry analyzer (TG8120, manufactured by Rigaku Corp.). The 5% weight-loss temperature measured at a temperature rise rate of 10° C./min was 317.1° C.

Example 7

(v) Preparation of Methyl n-butylbis(diethylamino)phosphonium bis(oxalato)borate In a 100 ml recovery flask equipped with a magnetic stirrer, 1.33 g (0.0033 mol) of methyl n-butylbis(diethylamino) phosphonium n-butyl sulfate obtained in (e) and 10 ml of acetonitrile were charged. While the resulting reaction mixture was stirred, a solution dissolving 0.64 g (0.0033 mol) of lithium bis(oxalato)borate in 30 ml of acetonitrile was added to the reaction mixture, and the resulting mixture was further stirred at room temperature for 2 days. The salt deposited was filtered off and vacuum-concentrated with a rotary evaporator. The resultant concentrate was dissolved in dichloromethane. After the resulting solution was washed with 100 ml of ultrapure water three times, the extracted solution was vacuum-concentrated with a rotary evaporator, and vacuum-dried at 80° C. In the form of a transparent liquid, 1.25 g of methyl n-butylbis(diethylamino)phosphonium bis(oxalato)borate was obtained; the yield was 87%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.08 (m, 8H)
2.22 (m, 2H)
1.91 (d, 3H)
1.46 (m, 4H)
1.16 (t, 12H)
0.94 (t, 3H)

$^{31}$P-NMR (121 MHz, solvent: $CDCl_3$, standard substance: triphenylphosphine)
δ 62.40 (m, 1P)

The structural formula is shown below (in the formula, the dashed line shows a conjugated structure).

[Chemical formula 26]

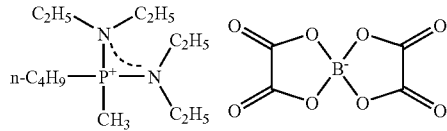

The melting point was measured with a differential scanning calorimeter (DSC8230, manufactured by Shimadzu Corp.). The glass transition temperature was −52.9° C. The thermal decomposition temperature was measured with a thermal gravimetry analyzer (TG8120, manufactured by Rigaku Corp.). The 5% weight-loss temperature measured at a temperature rise rate of 10° C./min was 284.3° C.

(w) Preparation of methyl n-butylbis(diethylamino)phosphonium trifluorosulfonate In a 30 ml recovery flask equipped with a magnetic stirrer, 0.50 g (0.0013 mol) of methyl n-butylbis(diethylamino) phosphonium n-butyl sulfate obtained in (e) was charged. With stirring, a solution dissolving 0.20 g (0.0014 mol) of lithium trifluorosulfonate in 10 ml of ultrapure water was further added. The resulting reaction mixture was further stirred at room temperature for 20 hours. After the water layer was removed, the reaction mixture was washed with ultrapure water three times, and then vacuum-dried at 80° C. In the form of a white solid, 0.23 g of methyl n-butylbis(diethylamino)phosphonium trifluorosulfonate was obtained; the yield was 46%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.12 (m, 8H)
2.33 (m, 2H)
2.02 (d, 3H)
1.50 (m, 4H)
1.19 (t, 12H)
0.97 (t, 3H)

$^{19}$F-NMR (282 MHz, solvent: $CDCl_3$, standard substance: $CF_3Cl$)
δ −78.28 (s, 3F)

$^{31}$P-NMR (121 MHz, solvent: $CDCl_3$, standard substance: triphenylphosphine)
δ 62.21 (m, 1P)

The structural formula is shown below (in the formula, the dashed line shows a conjugated structure).

[Chemical formula 27]

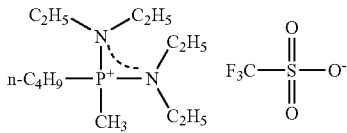

The melting point was measured with a differential scanning calorimeter (DSC8230, manufactured by Shimadzu Corp.). The melting point was 74.8° C. The glass transition temperature was 56.4° C. The thermal decomposition temperature was measured with a thermal gravimetry analyzer (TG8120, manufactured by Rigaku Corp.). The 5% weight-loss temperature measured at a temperature rise rate of 10° C./min was 311.8° C.

(x) Preparation of Methyl n-butylbis(diethylamino)phosphonium perfluoro-n-butyl sulfonate In a 30 ml recovery flask equipped with a magnetic stirrer, 0.50 g (0.0013 mol) of methyl n-butylbis(diethylamino)phosphonium n-butyl sulfate obtained in (e) was charged. With stirring, a solution dissolving 0.42 g (0.0014 mol) of lithium perfluoro n-butyl sulfonate in 5 ml of ultrapure water was further added. The resulting reaction mixture was further stirred at room temperature for 16 hours. After the water layer was removed, the reaction mixture was washed with ultrapure water three times, and then vacuum-dried at 80° C. In the form of a transparent liquid, 0.54 g of methyl n-butylbis(diethylamino)phosphonium perfluoro n-butyl sulfonate was obtained; the yield was 79%.

The resulting compound was identified with a nuclear magnetic resonance analyzer (BRUKER Ultra Shield 300

NMR Spectrometer, manufactured by BRUKER Limited). The resulting spectral data are shown below.

$^1$H-NMR (300 MHz, solvent: CDCl$_3$, standard substance: tetramethylsilane)

δ 3.12 (m, 8H)
2.32 (m, 2H)
2.02 (d, 3H)
1.49 (m, 4H)
1.18 (t, 12H)
0.97 (t, 3H)

$^{19}$F-NMR (282 MHz, solvent: CDCl$_3$, standard substance: CF$_3$Cl)

δ −80.91 (t-t, 3F)
−114.71 (m, 2F)
−121.63 (m, 2F)
−125.99 (m, 2F)

$^{31}$P-NMR (121 MHz, solvent: CDCl$_3$, standard substance: triphenylphosphine)

δ 64.09 (m, 1P)

The structural formula is shown below (in the formula, the dashed line shows a conjugated structure).

[Chemical formula 28]

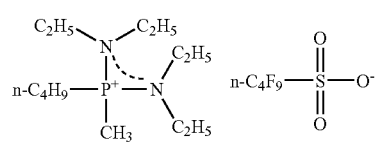

The melting point was measured with a differential scanning calorimeter (DSC8230, manufactured by Shimadzu Corp.). The melting point was 6.1° C. The crystallization temperature was −19.2° C. The thermal decomposition temperature was measured with a thermal gravimetry analyzer (TG8120, manufactured by Rigaku Corp.). The 5% weight-loss temperature measured at a temperature rise rate of 10° C./min was 328.8° C.

(y) Preparation of methyl n-butylbis(diethylamino)phosphonium pentafluoroethyl trifluoroborate In a 30 ml recovery flask equipped with a magnetic stirrer, 0.50 (0.0013 mol) of methyl n-butylbis(diethylamino)phosphonium n-butyl sulfate obtained in (e) was charged. With stirring, a solution dissolving 0.31 g (0.0014 mol) of potassium pentafluoroethyl trifluoroborate in 5 ml of ultrapure water was further added. The resulting reaction mixture was further stirred at room temperature for 20 hours. After the water layer was removed, the reaction mixture was washed with 100 ml of ultrapure water three times, and then vacuum-dried at 80° C. In the form of a white solid, 0.48 g of methyl n-butylbis(diethylamino)phosphonium pentafluoroethyl trifluoroborate was obtained; the yield was 88%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.10 (m, 8H)
2.22 (m, 2H)
1.91 (d, 3H)
1.48 (m, 4H)
1.17 (t, 12H)
0.97 (t, 3H)

$^{19}$F-NMR (282 MHz, solvent: CDCl$_3$, standard substance: CF$_3$Cl)

δ −83.80 (q, 3F)
−136.81 (q, 2F)
−154.33 (q, 2F)

$^{31}$P-NMR (121 MHz, solvent: CDCl$_3$, standard substance: triphenylphosphine)

δ 63.38 (m, 1P)

The structural formula is shown below (in the formula, the dashed line shows a conjugated structure).

[Chemical formula 29]

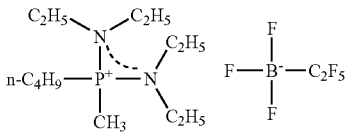

The melting point was measured with a differential scanning calorimeter (DSC8230, manufactured by Shimadzu Corp.). The melting point was 126.7° C. The crystallization temperature was 120.6° C. The thermal decomposition temperature was measured with a thermal gravimetry analyzer (TG8120, manufactured by Rigaku Corp.). The 5% weight-loss temperature measured at a temperature rise rate of 10° C./min was 289.6° C.

Example 8

(z) Preparation of chloro(N,N'-dimethyl-1,3-propylenediamino)phosphine

In a 1000 ml three-necked flask equipped with a dropping funnel and a magnetic stirrer, 4.2 ml (0.049 mol) of phosphorus trichloride and 300 ml of anhydrous diethyl ether were charged at room temperature in a nitrogen gas atmosphere, and the mixture was cooled to 5° C. or less in an ice bath. While the resulting reaction mixture was stirred, 5 g (0.049 mol) of N,N'-dimethyl-1,3-propylenediamine were slowly added dropwise to the reaction mixture. Furthermore, 14 ml (0.098 mol) of triethylamine were slowly added dropwise. After the reaction mixture was stirred at room temperature for 2 hours, the reaction mixture was filtered under pressure in a nitrogen gas atmosphere. The resulting crystals were washed with anhydrous diethyl ether three times, and then they were purified by vacuum-distillation (0.7 kPa, 90° C.), and 2.30 g of chloro(N,N'-dimethyl-1,3-propylenediamino)phosphine were obtained in the form of a transparent liquid; the yield was 29%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.00 (m, 4H)
2.68 (d, 6H)
1.90 (m, 2H)

$^{31}$P-NMR (121 MHz, solvent: CDCl$_3$, standard substance: triphenylphosphine)

δ 161.10 (s, 1P)

The structural formula is shown below.

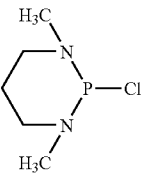

[Chemical formula 30]

(aa) Preparation of methyl(N,N'-dimethyl-1,3-propylenediamino)phosphine

In a 200 ml four-necked flask equipped with a refluxing condenser, a dropping funnel, and a magnetic stirrer, 2.30 g (0.014 mol) of chloro(N,N'-dimethyl-1,3-propylenediamino)phosphine obtained in (z) and 120 ml of anhydrous diethyl ether were charged at room temperature in a nitrogen gas atmosphere, and the mixture was cooled to −78° C. While the reaction mixture was stirred, 14 ml of a diethyl ether solution of 1 mol/L CH$_3$Li were added dropwise to the reaction mixture. While the reaction mixture was stirred, the temperature was elevated slowly, and then the reaction mixture was refluxed for 1 hour. After the temperature was returned back to room temperature, the resulting crystals were filtered off under pressure in a nitrogen gas atmosphere, and then washed with anhydrous diethyl ether three times. Furthermore, the crystals were purified by vacuum-distillation (5.0 kPa, 80° C.), and 1.11 g of methyl(N,N'-dimethyl-1,3-propylenediamino)phosphine were obtained in the form of a transparent liquid; the yield was 54%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.16 (m, 2H)
2.68 (m, 2H)
2.63 (d, 6H)
2.14 (m, 1H)
1.35 (m, 1H)
1.16 (d, 3H)

$^{31}$P-NMR (121 MHz, solvent: CDCl$_3$, standard substance: triphenylphosphine)

δ 90.09 (s, 1P)

The structural formula is shown below.

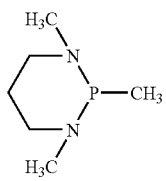

[Chemical formula 31]

(ab) Preparation of methyl n-butyl(N,N'-dimethyl-1,3-propylenediamino)phosphonium n-butyl sulfate In a 50 ml two-necked flask equipped with a magnetic stirrer, 0.80 g (0.0054 mol) of methyl(N,N'-dimethyl-1,3-propylenediamino)phosphine obtained in (aa) was charged at room temperature in a nitrogen gas atmosphere, ice-cooled, and then 1.1 ml (0.0054 mol) of di-n-butyl sulfate were added dropwise. After the resulting reaction mixture was stirred at 30° C. for 3 days, it was washed with diethyl ether three times. By vacuum drying at room temperature, 1.0 g of methyl n-butyl(N,N'-dimethyl-1,3-propylenediamino)phosphonium n-butyl sulfate was obtained in the form of a yellow liquid; the yield was 52%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 4.02 (t, 2H)
3.26 (m, 2H)
3.14 (m, 2H)
2.61 (d, 6H)
2.50 (m, 2H)
2.13 (d, 3H)
1.99 (m, 2H)
1.64 (m, 2H)
1.42 (m, 6H)
0.95 (m, 6H)

$^{31}$P-NMR (121 MHz, solvent: CDCl$_3$, standard substance: triphenylphosphine)

δ 71.32 (s, 1P)

The structural formula is shown below (in the formula, the dashed line shows a conjugated structure).

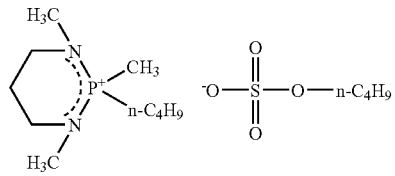

[Chemical formula 32]

(ac) Preparation of methyl n-butyl(N,N'-dimethyl-1,3-propylenediamino)phosphonium bistrifluoromethane sulfonylimide In a 50 ml recovery flask equipped with a magnetic stirrer, 1.00 g (0.0028 mol) of methyl n-butyl(N,N'-dimethyl-1,3-propylenediamino) phosphonium n-butyl sulfate obtained in (ab) and 10 ml of ultrapure water were charged. While the resulting reaction mixture was stirred, an aqueous solution dissolving 0.86 g (0.0030 mol) of LiTFSI in 10 ml of ultrapure water was added to the reaction mixture, and the resulting mixture was further stirred at room temperature for 20 hours. The resulting salt was extracted with 20 ml of CH$_2$Cl$_2$. The water layer was further extracted with 20 ml of CH$_2$Cl$_2$. The organic layer was washed with 20 ml of ultrapure water three times, and then the resulting extracted solution was concentrated with a rotary evaporator and vacuum-dried at 80° C. In the form of a yellow transparent liquid, 1.00 g of methyl n-butyl(N,N'-dimethyl-1,3-propylenediamino)phosphonium bistrifluoromethane sulfonylimide was obtained; the yield was 76%.

The resulting compound was identified with a nuclear magnetic resonance analyzer (BRUKER Ultra Shield 300

NMR Spectrometer, manufactured by BRUKER Limited). The resulting spectral data are shown below.

¹H-NMR (300 MHz, solvent: CDCl₃, standard substance: tetramethylsilane)
δ 3.22 (m, 4H)
2.76 (d, 6H)
2.28 (m, 2H)
2.01 (m, 2H)
1.88 (d, 3H)
1.46 (m, 4H)
0.97 (t, 6H)

¹⁹F-NMR (282 MHz, solvent: CDCl₃, standard substance: CF₃Cl)
δ −78.79 (s, 6F)

³¹P-NMR (121 MHz, solvent: CDCl₃, standard substance: triphenylphosphine)
δ 69.52 (m, 1P)

The structural formula is shown below (in the formula, the dashed line shows a conjugated structure).

[Chemical formula 33]

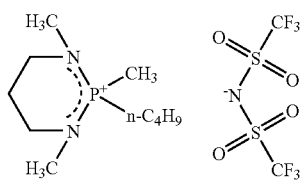

The melting point was measured with a differential scanning calorimeter (DSC8230, manufactured by Shimadzu Corp.). The melting point was 36.2° C. The crystallization temperature was −24.6° C. The thermal decomposition temperature was measured with a thermal gravimetry analyzer (TG8120, manufactured by Rigaku Corp.). The 5% weight-loss temperature measured at a temperature rise rate of 10° C./min was 285.5° C.

Example 9

(ad) Preparation of dichloro(N-methylethylamino)oxophosphorus

In a 1000 ml three-necked flask equipped with a dropping funnel and a magnetic stirrer, 19 ml (0.208 mol) of phosphoryl chloride and 400 ml of anhydrous diethyl ether were charged at room temperature in a nitrogen gas atmosphere, and the mixture was cooled to 5° C. or less in an ice bath. While the resulting reaction mixture was stirred, 18.1 ml (0.208 mol) of N-methylethylamine were slowly added dropwise to the reaction mixture. Furthermore, 29 ml (0.208 mol) of triethylamine were added dropwise. After the reaction mixture was stirred for 1 hour while it was ice-cooled, the reaction mixture was filtered under pressure in a nitrogen gas atmosphere. The resulting crystals were washed with anhydrous diethyl ether three times, and then they were purified by vacuum-distillation (1.3 kPa, 80° C.), and 32.68 g of dichloro(N-methylethylamino)oxophosphorus in the form of a transparent liquid; the yield was 89%.

The resulting compound was identified with a nuclear magnetic resonance analyzer (BRUKER Ultra Shield 300 NMR Spectrometer, manufactured by BRUKER Limited). The resulting spectral data are shown below.

¹H-NMR (300 MHz, solvent: CDCl₃, standard substance: tetramethylsilane)
δ 3.32 (m, 2H)
2.86 (d, 3H)
1.24 (t, 3H)

³¹P-NMR (121 MHz, solvent: CDCl₃, standard substance: triphenylphosphine)
δ 17.88 (m, 1P)

The structural formula is shown below.

[Chemical formula 34]

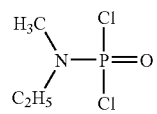

(ae) Preparation of dimethyl(N-methylethylamino)oxophosphorus

In a 300 ml four-necked flask equipped with a refluxing condenser, a dropping funnel, and a magnetic stirrer, 15.00 g (0.08500 mol) of dichloro(N-methylethylamino)oxophosphorus obtained in (ad) and 100 ml of anhydrous diethyl ether were charged at room temperature in a nitrogen gas atmosphere, and the mixture was cooled to −78° C. While the reaction mixture was stirred, 57 ml of a diethyl ether solution of 3 mol/L CH₃MgBr were added dropwise to the reaction mixture. After the reaction mixture was stirred for 15 minutes, the temperature was elevated slowly, and then the reaction mixture was refluxed for 3 hours. After the temperature was returned back to room temperature, the resulting crystals were filtered off under pressure in a nitrogen gas atmosphere, and then washed with anhydrous diethyl ether three times. Furthermore, the crystals were purified by vacuum-distillation (0.1 kPa, 50-55° C.), and 1.42 g of dimethyl(N-methylethylamino)oxophosphorus were obtained in the form of a transparent liquid; the yield was 12%.

The resulting compound was identified with a nuclear magnetic resonance analyzer (BRUKER Ultra Shield 300 NMR Spectrometer, manufactured by BRUKER Limited). The resulting spectral data are shown below.

¹H-NMR (300 MHz, solvent: CDCl₃, standard substance: tetramethylsilane)
δ 3.02 (m, 2H)
2.63 (d, 3H)
1.46 (d, 6H)
1.14 (t, 3H)

³¹P-NMR (121 MHz, solvent: CDCl₃, standard substance: triphenylphosphine)
δ 43.28 (m, 1P)

The structural formula is shown below.

[Chemical formula 35]

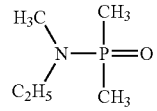

(af) Preparation of dimethyl(N-methylethylamino)n-butoxyphosphonium n-butyl sulfate In a 50 ml two-necked flask equipped with a magnetic stirrer, at room temperature in a nitrogen gas atmosphere, 1.42 g (0.0105 mol) of dimethyl(N-methylethylamino)oxophosphorus obtained in (ae) were charged and ice-cooled. Subsequently, 2.5 ml (0.0126 mol) of di-n-butyl sulfate were added dropwise. The resulting reaction mixture was stirred at 30° C. for 7 days, and then it was washed with diethyl ether three times and vacuum-dried at room temperature, and 2.59 g of dimethyl(N-methylethylamino) n-butoxyphosphonium n-butyl sulfate were obtained in the form of a white solid; the yield was 71%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: acetone-$d_6$, standard substance: tetramethylsilane)

δ 4.24 (m, 2H)

3.84 (t, 2H)

3.34 (m, 2H)

2.96 (d, 3H)

2.32 (d, 6H)

1.73-1.34 (m, 8H)

1.25 (t, 3H)

0.99-0.88 (m, 6H)

$^{31}$P-NMR (121 MHz, solvent: acetone-$d_6$, standard substance: triphenylphosphine)

δ 80.00 (m, 1P)

The structural formula is shown below.

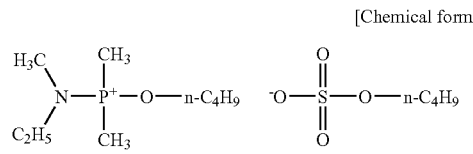

[Chemical formula 36]

(ag) Preparation of dimethyl(N-methylethylamino)n-butoxyphosphonium bistrifluoromethane sulfonylimide In a 50 ml recovery flask equipped with a magnetic stirrer, 2.59 g (0.0075 mol) of dimethyl(N-methylethylamino)$_n$-butoxyphosphonium n-butyl sulfate obtained in (af) were charged. An aqueous solution dissolving 2.6 g (0.0090 mol) of LiTFSI in 25 ml of ultrapure water was added with stirring. The resulting reaction mixture was further stirred at room temperature for 14 hours. The resulting salt was extracted with 50 ml of $CH_2Cl_2$, and the water layer was further extracted with 50 ml of $CH_2Cl_2$. The organic layer was washed with 100 ml of ultrapure water three times, and then the resulting extracted solution was concentrated with a rotary evaporator and vacuum-dried at 80° C. In the form of a transparent liquid, 2.94 g of dimethyl(N-methylethylamino) n-butoxyphosphonium bistrifluoromethane sulfonylimide were obtained; the yield was 83%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 4.03 (quart, 2H)

3.29 (m, 2H)

2.85 (d, 3H)

2.05 (d, 6H)

1.68 (m, 2H)

1.39 (m, 2H)

1.23 (t, 3H)

0.94 (t, 3H)

$^{19}$F-NMR (282 MHz, solvent: $CDCl_3$, standard substance: $CF_3Cl$)

δ -78.99 (s, 6F)

$^{31}$P-NMR (121 MHz, solvent: $CDCl_3$, standard substance: triphenylphosphine)

δ 76.98 (m, 1P)

The structural formula is shown below.

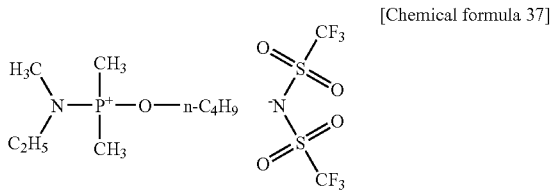

[Chemical formula 37]

The melting point was measured with a differential scanning calorimeter (DSC8230, manufactured by Shimadzu Corp.). The glass transition temperature was −88.7° C. The thermal decomposition temperature was measured with a thermal gravimetry analyzer (TG8120, manufactured by Rigaku Corp.). The 5% weight-loss temperature measured at a temperature rise rate of 10° C./min was 217.2° C.

Example 10

B(a) Preparation of tris(diethylamino)phosphoimine hydrochloride

In a 500 ml three-necked flask equipped with a refluxing condenser, a dropping funnel, and a magnetic stirrer, 20.0 g (0.146 mol) of phosphorus trichloride and 185 ml (1.91 mol) of carbon tetrachloride were charged at room temperature in a nitrogen gas atmosphere, and the mixture was cooled to 5° C. or less in an ice bath. Subsequently, 91.5 ml (0.884 mol) of diethylamine were slowly added dropwise at 30° C. with stirring. After the temperature became constant, the resulting reaction mixture was further stirred for 1 hour at room temperature so as to obtain a yellow liquid. Then, anhydrous ammonia was bubbled from the bottom of the liquid at 25° C. for about 1.5 hours so as to obtain a faint yellow suspension. After bubbling, the suspension was further stirred overnight. The suspension was filtered off, and the resulting residue was washed with 10 ml of carbon tetrachloride. The filtrate obtained was vacuum-distilled to remove the solvent. Tris (diethylamino)phosphoimine hydrochloride was obtained in the form of a honey-like yellow viscous liquid.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 9.88 (broad, 1H)

3.13 (m, 12H)

1.17 (t, 18H)

$^{31}$P-NMR (121 MHz, solvent: $CDCl_3$, standard substance: triphenylphosphine)

δ 41.34 (m, 1P)

The structural formula is shown below.

[Chemical formula 38]

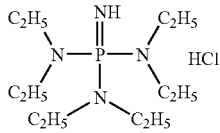

B(b) Preparation of tris(diethylamino)dimethylaminophosphonium iodide

In a 100 ml three-necked flask equipped with a refluxing condenser and a magnetic stirrer, 7.26 g (about 0.0243 mol) of crude tris(diethylamino)phosphoimine hydrochloride obtained in B(a) were charged, and an aqueous solution dissolving 2.33 g (0.0583 mol) of NaOH in 2.5 ml of ultrapure water was slowly added dropwise. An orange-colored suspension was obtained after 1 hour stirring at room temperature. Subsequently, an aqueous solution dissolving 2.59 g (0.0648 mol) of NaOH in 10 ml of ultrapure water and 7.1 ml (0.011 mol) of iodomethane were added, and the resulting reaction solution was stirred at 70° C. for 15 hours.

After the temperature was returned back to room temperature, the reaction solution separating into two layers was extracted with 30 ml of $CH_2Cl_2$. The water layer was further extracted with $CH_2Cl_2$ twice. The extract together with the organic layer was dried with anhydrous $Na_2SO_4$, filtered, vacuum-distilled to remove most of the solvent, washed with ether three times, and vacuum-dried at 90° C. to obtain 9.9 g of a brown-colored oily product (the yield was 97% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.20 (m, 12H)
2.87 (s, 6H)
1.25 (t, 18H)
$^{31}$P-NMR (121 MHz, solvent: $CDCl_3$, standard substance: triphenylphosphine)
δ 43.12 (m, 1P)

The structural formula is shown below (in the formula, the dashed lines show a conjugated structure).

[Chemical formula 39]

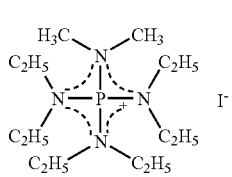

B(c) Preparation of tris(diethylamino)dimethylaminophosphonium bistrifluoromethane sulfonylimide In 10 ml of $CH_2Cl_2$, 9.9 g (0.0236 mol) of tris(diethylamino)dimethylaminophosphonium iodide obtained in B(b) were dissolved, which was then back-extracted with 150 ml of ultrapure water three times. To the aqueous solutions obtained in the second and third back-extractions, an aqueous solution dissolving 6.8 g (0.024 mol) of LiTFSI in 30 ml of ultrapure water was added, and then the resultant mixture was stirred at room temperature for 1 hour. The resulting salt was extracted with 100 ml of $CH_2Cl_2$, and the water layer was further extracted with 100 ml of $CH_2Cl_2$ twice. After washing twice with ultrapure water, the resulting extracted solution was concentrated with a rotary evaporator and vacuum-dried at 90° C. so as to obtain 4.55 g of a product; the yield was 34.7%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.13 (m, 12H)
2.77 (s, 6H)
1.21 (t, 18H)
$^{19}$F-NMR (282 MHz, solvent: $CDCl_3$, standard substance: $CF_3Cl$)
δ −78.79 (s, 6F)
$^{31}$P-NMR (121 MHz, solvent: $CDCl_3$, standard substance: triphenylphosphine)
δ 41.34 (m, 1P)

The structural formula is shown below (in the formula, the dashed lines show a conjugated structure).

[Chemical formula 40]

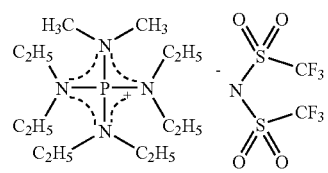

The melting point was measured with a differential scanning calorimeter (DSC8230, manufactured by Shimadzu Corp.). The melting point was 119.8° C. The thermal decomposition temperature was measured with a thermal gravimetry analyzer (TG8120, manufactured by Rigaku Corp.). The 5% weight-loss temperature measured at a temperature rise rate of 10° C./min was 359.1° C.

Example 11

B(d) Preparation of tetrakis(diethylamino)phosphonium bromide

In a 100 ml three-necked flask equipped with a refluxing condenser and a magnetic stirrer, 7.26 g (about 0.0243 mol) of crude tris(diethylamino)phosphoimine hydrochloride obtained in B(a) were charged, and an aqueous solution dissolving 2.33 g (0.0583 mol) of NaOH in 2.5 ml of ultrapure water was slowly added dropwise. An orange-colored suspension was obtained after 1 hour stirring at room temperature. Subsequently, an aqueous solution dissolving 1.16 g (0.0291 mol) of NaOH in 5 ml of ultrapure water and 4.3 ml (0.057 mol) of bromoethane were added, and the resulting reaction solution was stirred at 70° C. for 25 hours.

After the temperature was returned back to room temperature, the reaction solution separating into two layers was extracted with 10 ml of $CH_2Cl_2$, and the water layer was further extracted with CH$_2$Cl$_2$ twice. The extract together with the organic layer were dried with anhydrous Na$_2$SO$_4$, filtered, vacuum-distilled to remove most of the solvent, washed with ether three times, and vacuum-dried at 90° C. to obtain 7.18 g of a brown-colored oily product (the yield was 71% based on PCl$_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.20 (m, 16H)

1.25 (t, 24H)

$^{31}$P-NMR (121 MHz, solvent: CDCl$_3$, standard substance: triphenylphosphine)

δ 44.03 (m, 1P)

The structural formula is shown below (in the formula, the dashed lines show a conjugated structure).

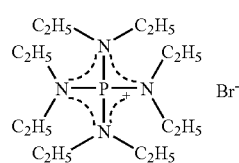

[Chemical formula 41]

B(e) Preparation of tetrakis(diethylamino)phosphonium bistrifluoromethane sulfonylimide In 5 ml of CH$_2$Cl$_2$, 13.7 g (0.0343 mol) of tetrakis(diethylamino)phosphonium bromide obtained in B(d) were dissolved, which was then back-extracted with 70 ml of ultrapure water. To the aqueous solution obtained in the back-extraction, an aqueous solution dissolving 10.0 g (0.0348 mol) of LiTFSI in 50 ml of ultrapure water was added, and then the resultant mixture was stirred at room temperature for 1 hour. The resulting salt was extracted with 70 ml of CH$_2$Cl$_2$, and the water layer was further extracted with 20 ml of CH$_2$Cl$_2$. After washing twice with 70 ml of ultrapure water, the resulting extracted solution was concentrated with a rotary evaporator and vacuum-dried at 90° C. so as to obtain 14.22 g of a product; the yield was 97.3% based on PCl$_3$.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.14 (m, 16H)

1.21 (t, 24H)

$^{19}$F-NMR (282 MHz, solvent: CDCl$_3$, standard substance: CF$_3$Cl)

δ −78.80 (s, 6F)

$^{31}$P-NMR (121 MHz, solvent: CDCl$_3$, standard substance: triphenylphosphine)

δ 43.96 (m, 1P)

The structural formula is shown below (in the formula, the dashed lines show a conjugated structure).

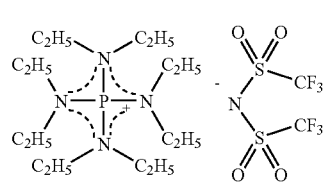

[Chemical formula 42]

The melting point was measured with a differential scanning calorimeter (DSC8230, manufactured by Shimadzu Corp.). No peak, which can be recognized as a melting point, was observed. By visual observation, melting started at 90° C. The thermal decomposition temperature was measured with a thermal gravimetry analyzer (TG8120, manufactured by Rigaku Corp.). The 5% weight-loss temperature measured at a temperature rise rate of 10° C./min was 376.0° C.

Example 12

B(f) Preparation of tris(diethylamino)di-n-propylaminophosphonium iodide

In a 100 ml three-necked flask equipped with a refluxing condenser and a magnetic stirrer, 10.0 g (about 0.0335 mol) of crude tris(diethylamino) phosphoimine hydrochloride obtained in B(a) were charged, and an aqueous solution dissolving 2.68 g (0.0670 mol) of NaOH in 3 ml of ultrapure water was slowly added dropwise. An orange-colored suspension was obtained after 1 hour stirring at room temperature. Subsequently, an aqueous solution dissolving 5.51 g (0.138 mol) of NaOH in 20 ml of ultrapure water and 26 ml (0.238 mol) of iodo-n-propane were added, and the resulting reaction mixture was stirred at 70° C. for 19 hours.

After the temperature was returned back to room temperature, the reaction mixture separating into two layers was extracted with 50 ml of CH$_2$Cl$_2$, and the water layer was further extracted with CH$_2$Cl$_2$. The extract together with the organic layer were dried with anhydrous Na$_2$SO$_4$, filtered, vacuum-distilled to remove most of the solvent, washed with ether three times, and vacuum-dried at 90° C. to obtain 16.47 g of a brown-colored oily product.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.19 (m, 12H)

2.99 (m, 4H)

1.62 (m, 4H)

1.23 (t, 18H)

0.96 (t, 6H)

$^{31}$P-NMR (121 MHz, solvent: CDCl$_3$, standard substance: triphenylphosphine)

δ 43.61 (m, 1P)

The structural formula is shown below (in the formula, the dashed lines show a conjugated structure).

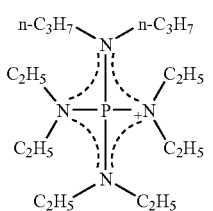

[Chemical formula 43]

B(g) Preparation of tis(diethylamino)di-n-propylaminophosphonium bistrifluoromethane sulfonylimide In 5 ml of $CH_2Cl_2$, 16.47 g (0.0347 mol) of tris(diethylamino)di-n-propylaminophosphonium iodide obtained in B(f) were dissolved, which was then back-extracted with 50 ml of ultrapure water five times. To the aqueous solutions obtained in the third, forth, and fifth back-extractions, an aqueous solution dissolving 10.0 g (0.035 mol) of LiTFSI in 50 ml of ultrapure water was added, and then the resultant mixture was stirred at 50° C. for 4 days. The resulting salt was extracted with 150 ml of $CH_2Cl_2$, and the water layer was further extracted with 50 ml of $CH_2Cl_2$. After washing twice with ultrapure water, the resulting extracted solution was concentrated with a rotary evaporator and vacuum-dried at 90° C. so as to obtain 4.42 g of a product; the yield was 20.3% based on $PCl_3$.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ3.14 (m, 12H)
2.95 (m, 4H)
1.60 (m, 4H)
1.22 (t, 18H)
0.93 (t, 6H)
$^{19}$F-NMR (282 MHz, solvent: $CDCl_3$, standard substance: $CF_3Cl$)
δ −78.75 (s, 6F)
$^{31}$P-NMR (121 MHz, solvent: $CDCl_3$, standard substance: triphenylphosphine)
δ 43.96 (m, 1P)

The structural formula is shown below (in the formula, the dashed lines show a conjugated structure).

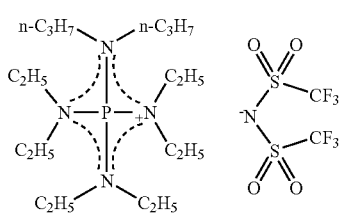

[Chemical formula 44]

The melting point was measured with a differential scanning calorimeter (DSC8230, manufactured by Shimadzu Corp.). The melting point was 94.1° C. The thermal decomposition temperature was measured with a thermal gravimetry analyzer (TG8120, manufactured by Rigaku Corp.). The 5% weight-loss temperature measured at a temperature rise rate of 10° C./min was 362.0° C.

Example 13

B(h) Preparation of tris(diethylamino)di-n-butylaminophosphonium iodide

In a 100 ml three-necked flask equipped with a refluxing condenser and a magnetic stirrer, 42.4 g (about 0.142 mol) of crude tris(diethylamino)phosphoimine hydrochloride obtained in B(a) were charged, and an aqueous solution dissolving 11.68 g (0.292 mol) of NaOH in 12 ml of ultrapure water was slowly added dropwise. An orange-colored suspension was obtained after 1 hour stirring at room temperature. Subsequently, an aqueous solution dissolving 23.36 g (0.586 mol) of NaOH in 90 ml of ultrapure water and 118 ml (0.238 mol) of iodo-n-butane were added, and the resulting reaction mixture was stirred at 70° C. for 19 hours.

After the temperature was returned back to room temperature, the reaction mixture separating into two layers was separated. The organic layer was washed with ultrapure water five times, vacuum-distilled to remove most of the solvent, vacuum-dried at 70° C., further washed with ether three times, vacuum-distilled again to remove most of the solvent, and dried at 70° C. to obtain 42.58 g of a brown-colored oily product (the yield was 59.7% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.19 (m, 12H)
3.02 (m, 4H)
1.56 (m, 4H)
1.35 (m, 4H)
1.25 (t, 18H)
0.98 (t, 6H)
$^{31}$P-NMR (121 MHz, solvent: $CDCl_3$, standard substance: triphenylphosphine)
δ 43.74 (m, 1P)

The structural formula is shown below (in the formula, the dashed lines show a conjugated structure).

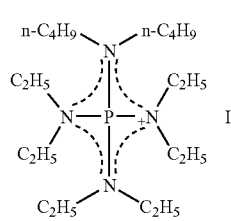

[Chemical formula 45]

B(i) Preparation of tris(diethylamino)di-n-butylaminophosphonium bistrifluoromethane sulfonylimide To 48.75 g (0.097 mol) of tris(diethylamino)di-n-butylaminophosphonium iodide obtained in B(h), an aqueous solution dissolving 28.7 g (0.100 mol) of LiTFSI in 200 ml of ultrapure water was added, and then the resultant mixture was stirred at 50° C. for 3 days. The resulting salt was extracted with 100 ml of $CH_2Cl_2$, and the water layer was further extracted with 50 ml of $CH_2Cl_2$. After five times of washing with ultrapure water, the resulting extracted solution was concentrated with a rotary evaporator and vacuum-dried at 90° C., and then passed through an alumina column (developing solvent: $CH_2Cl_2$). The extracted solution was concentrated again with a rotary evaporator and vacuum-dried at 90° C. so as to obtain 54.59 g of a product; the yield was 85.8%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.14 (m, 12H)
2.99 (m, 4H)
1.54 (m, 4H)
1.33 (m, 4H)
1.22 (t, 18H)
0.97 (t, 6H)

$^{19}$F-NMR (282 MHz, solvent: $CDCl_3$, standard substance: $CF_3Cl$)

δ −78.75 (s, 6F)

$^{31}$P-NMR (121 MHz, solvent: $CDCl_3$, standard substance: triphenylphosphine)

δ 43.85 (m, 1P)

The structural formula is shown below (in the formula, the dashed lines show a conjugated structure).

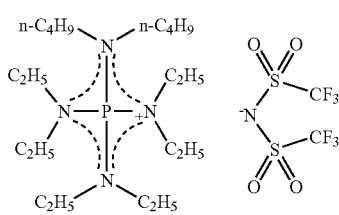

[Chemical formula 46]

The melting point was measured with a differential scanning calorimeter (DSC8230, manufactured by Shimadzu Corp.). The melting point was 25.4° C. The thermal decomposition temperature was measured with a thermal gravimetry analyzer (TG8120, manufactured by Rigaku Corp.). The 5% weight-loss temperature measured at a temperature rise rate of 10° C./min was 362.5° C.

The electrical conductivity as measured with the AC impedance method (Electrochemical Measurement System HZ-3000, manufactured by Hokuto Denko Corp.) was 0.0642 $Sm^{-1}$ at 50° C.

The potential window was −0.1 V to 4.8 V with respect to Li/Li$^+$, which was obtained from a cyclic voltammogram measured with the Electrochemical Measurement System HZ-3000 manufactured by Hokuto Denko Corp. using Pt for a working electrode and a counter electrode and Li for a reference electrode. A CV curve of tris(diethylamino)di-n-butylaminophosphonium bistrifluoromethane sulfonylimide is shown in FIG. 3.

To 3.8 g (0.0058 mol) of tris(diethylamino)di-n-butylaminophosphonium bistrifluoromethane sulfonyl imide, an aqueous solution dissolving 5 g of NaOH in 20 ml of $H_2O$ was added, and then the resulting reaction mixture was stirred at 50° C. for 14 hours. Subsequently, 50 ml of $CH_2Cl_2$ were added to the reaction mixture, and the resultant solution was separated. The organic layer was washed with 30 ml of ultrapure water three times, vacuum-concentrated, and vacuum-dried at 80° C. so as to obtain 3.7 g of a product; the yield was 96%.

A similar experiment was carried out using ethylmethylimidazolium bistrifluoromethane sulfonylimide; the yield was 81%.

B(j) Preparation of tris(diethylamino)di-n-butylaminophosphonium nitrate

In 20 ml of $CH_2Cl_2$, 2.48 g (0.00494 mol) of tris(diethylamino) di-n-butylaminophosphonium iodide obtained in B(h) were dissolved. To the resulting solution, 20 ml of an aqueous solution dissolving 0.87 g of $AgNO_3$ were added. The resulting crystals were filtered off. The filtrate was washed with ultrapure water twice, concentrated with a rotary evaporator, and vacuum-dried at 80° C. so as to obtain 1.47 g of a product; the yield was 67.9%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.17 (m, 12H)
3.01 (m, 4H)
1.55 (m, 4H)
1.33 (m, 4H)
1.24 (t, 18H)
0.97 (t, 6H)

$^{31}$P-NMR (121 MHz, solvent: $CDCl_3$, standard substance: triphenylphosphine)

δ 43.81 (m, 1P)

The structural formula is shown below (in the formula, the dashed lines show a conjugated structure).

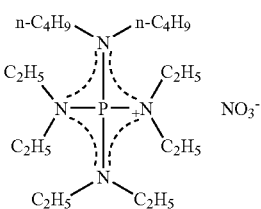

[Chemical formula 47]

The melting point was measured with a differential scanning calorimeter (DSC8230, manufactured by Shimadzu Corp.). The melting point was 61.2° C. The thermal decomposition temperature was measured with a thermal gravimetry analyzer (TG8120, manufactured by Rigaku Corp.). The 5% weight-loss temperature measured at a temperature rise rate of 10° C./min was 282.8° C.

Example 14

B(k) Preparation of tris(N-methyl-n-butylamino)phosphoimine hydrochloride

In a 500 ml three-necked flask equipped with a refluxing condenser, a dropping funnel, and a magnetic stirrer, 10.0 g (0.0728 mol) of phosphorus trichloride and 92 ml (0.954 mol) of carbon tetrachloride were charged at room temperature in a nitrogen gas atmosphere, and the mixture was cooled to 5° C. or less in an ice bath. Subsequently, 52 ml (0.442 mol) of N-methyl-n-butylamine were slowly added dropwise at 30° C. or less with stirring. After the temperature became constant, the resulting reaction mixture was further stirred for 1 hour at room temperature so as to obtain a yellow liquid. Then, anhydrous ammonia was bubbled from the bottom of the liquid at 25° C. so as to obtain a faint yellow suspension. After bubbling, the suspension was further stirred overnight. The suspension was filtered off, and the resulting residue was washed with 10 ml of carbon tetrachloride. The filtrate obtained was vacuum-distilled to remove the solvent. In the form of a honey-like yellow viscous liquid, 27.30 g of tris(N-methyl-n-butylamino) phosphoimine hydrochloride were obtained.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 9.89 (broad, 1H)

2.98 (m, 6H)

2.76 (d, 9H)

1.59 (m, 6H)

1.33 (m, 6H)

0.94 (t, 9H)

$^{31}$P-NMR (121 MHz, solvent: CDCl$_3$, standard substance: triphenylphosphine)

δ 41.56 (m, 1P)

The structural formula is shown below.

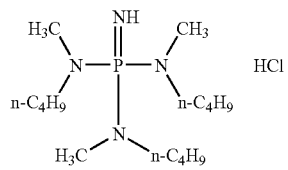

[Chemical formula 48]

B(l) Preparation of tris(N-methyl-n-butylamino)dimethylaminophosphonium iodide

In a 100 ml three-necked flask equipped with a refluxing condenser and a magnetic stirrer, 5.00 g (about 0.0134 mol) of crude tris(N-methyl-n-butylamino) phosphoimine hydrochloride obtained in B(k) were charged, and an aqueous solution dissolving 1.07 g (0.0268 mol) of NaOH in 1 ml of ultrapure water was slowly added dropwise. An orange-colored suspension was obtained after 1 hour stirring at room temperature. Subsequently, an aqueous solution dissolving 2.68 g (0.067 mol) of NaOH in 10 ml of ultrapure water and 6 ml (0.09 mol) of iodomethane were added, and the resulting reaction mixture was stirred at 70° C. for 3.5 hours.

After the temperature was returned back to room temperature, 50 ml of CH$_2$Cl$_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 4.75 g of a brown-colored oily product (the yield was 74.7% based on PCl$_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 2.96 (m, 6H)

2.84 (d, 15H)

1.59 (m, 6H)

1.34 (m, 6H)

0.97 (t, 9H)

$^{31}$P-NMR (121 MHz, solvent: CDCl$_3$, standard substance: triphenylphosphine)

δ 42.89 (m, 1P)

The structural formula is shown below (in the formula, the dashed lines show a conjugated structure).

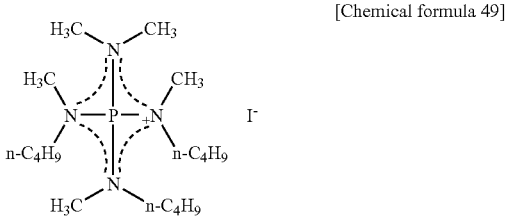

[Chemical formula 49]

B(m) Preparation of tris(N-methyl-n-butylamino) dimethylaminophosphonium bistrifluoromethane sulfonyl imide To 4.75 g (0.010 mol) of tris(N-methyl-n-butylamino)dimethylaminophosphonium iodide obtained in B(l), an aqueous solution dissolving 3.2 g (0.011 mol) of LiTFSI in 50 ml of ultrapure water was added, and the resultant solution was stirred at 50° C. for 19 hours. The resulting salt was extracted with 100 ml of CH$_2$Cl$_2$ and washed with ultrapure water three times. The extracted solution was concentrated with a rotary evaporator, vacuum-dried at 80° C. to obtain 5.35 g of a product; the yield was 87.2%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 2.90 (m, 6H)

2.76 (d, 9H)

2.74 (d, 6H)

1.57 (m, 6H)

1.32 (m, 6H)

0.96 (t, 9H)

$^{19}$F-NMR (282 MHz, solvent: CDCl$_3$, standard substance: CF$_3$Cl)

δ −78.84 (s, 6F)

$^{31}$P-NMR (121 MHz, solvent: CDCl$_3$, standard substance: triphenylphosphine)

δ 43.85 (m, 1P)

The structural formula is shown below (in the formula, the dashed lines show a conjugated structure).

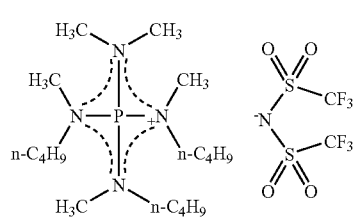

[Chemical formula 50]

The melting point was measured with a differential scanning calorimeter (DSC8230, manufactured by Shimadzu Corp.). No peak, which can be recognized as a melting point, was observed. The compound was visually in the form of a liquid at a room temperature of 20° C. The thermal decomposition temperature was measured with a thermal gravimetry analyzer (TG8120, manufactured by Rigaku Corp.). The 5% weight-loss temperature measured at a temperature rise rate of 10° C./min was 395.0° C.

Example 15

B(n) Preparation of tris(N-methyl-n-butylamino)diethylaminophosphonium iodide

In a 100 ml three-necked flask equipped with a refluxing condenser and a magnetic stirrer, 5.53 g (about 0.0147 mol) of crude tris(N-methyl-n-butylamino) phosphoimine hydrochloride obtained in B(k) were charged, and an aqueous solution dissolving 1.18 g (0.0295 mol) of NaOH in 1 ml of ultrapure water was slowly added dropwise. An orange-colored suspension was obtained after 1 hour stirring at room temperature. Subsequently, an aqueous solution dissolving 2.95 g (0.0737 mol) of NaOH in 10 ml of ultrapure water and 8.5 ml (0.10 mol) of iodomethane were added, and the resulting reaction mixture was stirred at 70° C. for 15.5 hours.

After the temperature was returned back to room temperature, 50 ml of $CH_2Cl_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 5.41 g of a brown-colored oily product (the yield was 75.3% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.16 (m, 4H)

2.97 (m, 6H)

2.84 (d, 9H)

1.59 (m, 6H)

1.34 (m, 6H)

1.25 (t, 6H)

0.97 (t, 9H)

$^{31}$P-NMR (121 MHz, solvent: $CDCl_3$, standard substance: triphenylphosphine)

δ 43.26 (m, 1P)

The structural formula is shown below (in the formula, the dashed lines show a conjugated structure).

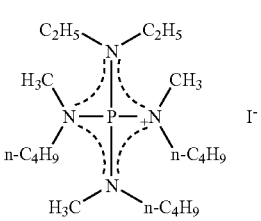

[Chemical formula 51]

B(o) Preparation of tris(N-methyl-n-butylamino)diethylaminophosphonium bistrifluoromethane sulfonylimide To 5.41 g (0.011 mol) of tris(N-methyl-n-butylamino)diethylaminophosphonium iodide obtained in B(n), an aqueous solution dissolving 3.5 g (0.012 mol) of LiTFSI in 50 ml of ultrapure water was added, and the resultant solution was stirred at 50° C. for 23 hours. The resulting salt was extracted with 100 ml of $CH_2Cl_2$ and washed with ultrapure water three times. The extracted solution was concentrated with a rotary evaporator, vacuum-dried at 80° C. to obtain 6.43 g of a product; the yield was 90.3%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.10 (m, 4H)

2.91 (m, 6H)

2.76 (d, 9H)

1.57 (m, 6H)

1.33 (m, 6H)

1.22 (t, 6H)

0.96 (t, 9H)

$^{19}$F-NMR (282 MHz, solvent: $CDCl_3$, standard substance: $CF_3Cl$)

δ −78.82 (s, 6F)

$^{31}$P-NMR (121 MHz, solvent: $CDCl_3$, standard substance: triphenylphosphine)

δ 43.44 (m, 1P)

The structural formula is shown below (in the formula, the dashed lines show a conjugated structure).

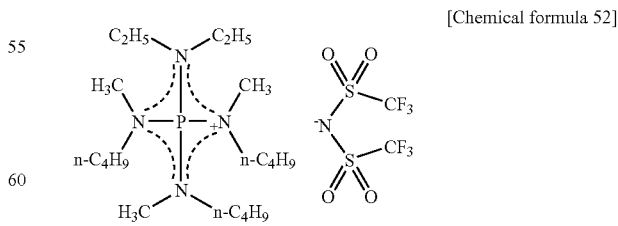

[Chemical formula 52]

The melting point was measured with a differential scanning calorimeter (DSC8230, manufactured by Shimadzu Corp.). The melting point was 3.7° C. The thermal decomposition temperature was measured with a thermal gravimetry analyzer (TG8120, manufactured by Rigaku Corp.). The 5% weight-loss temperature measured at a temperature rise rate of 10° C./min was 402.1° C.

Example 16

B(p) Preparation of tris(N-methyl-n-butylamino)di-n-propylaminophosphonium iodide In a 100 ml three-necked flask equipped with a refluxing condenser and a magnetic stirrer, 0.90 g (about 0.0025 mol) of crude tris(N-methyl-n-butylamino) phosphoimine hydrochloride obtained in B(k) was charged, and an aqueous solution dissolving 0.20 g (0.0050 mol) of NaOH in 0.5 ml of ultrapure water was slowly added dropwise. An orange-colored suspension was obtained after 1 hour stirring at room temperature. Subsequently, an aqueous solution dissolving 0.50 g (0.0125 mol) of NaOH in 2 ml of ultrapure water and 1.70 ml (0.0175 mol) of iodo-n-propane were added, and the resulting reaction mixture was stirred at 70° C. for 15.5 hours.

After the temperature was returned back to room temperature, 50 ml of $CH_2Cl_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 0.93 g of tris (N-methyl-n-butylamino)di-n-propylaminophosphonium iodide (the yield was 76% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 2.96 (m, 10H)
2.83 (d, 9H)
1.60 (m, 10H)
1.25 (m, 6H)
0.97 (m, 15H)
$^{31}$P-NMR (121 MHz, solvent: $CDCl_3$, standard substance: triphenylphosphine)
δ 43.13 (m, 1P)

The structural formula is shown below (in the formula, the dashed lines show a conjugated structure).

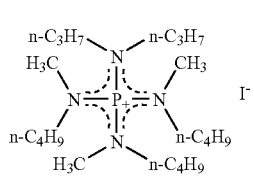

[Chemical formula 53]

B(q) Preparation of tris(N-methyl-n-butylamino)di-n-propylaminophosphonium bistrifluoromethane sulfonylimide To 0.93 g (0.0018 mol) of tris(N-methyl-n-butylamino)di-n-propylaminophosphonium iodide obtained in B(p), an aqueous solution dissolving 0.6 g (0.002 mol) of LiTFSI in 15 ml of ultrapure water was added, and the resulting solution was stirred at 50° C. for 39 hours. The resulting salt was extracted with 100 ml of $CH_2Cl_2$ and washed with ultrapure water three times. The extracted solution was concentrated with a rotary evaporator, vacuum-dried at 80° C. to obtain 0.52 g of tis(N-methyl-n-butylamino)di-n-propylaminophosphonium bistrifluoromethane sulfonylimide; the yield was 43%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 2.91 (m, 10H)
2.75 (d, 9H)
1.58 (m, 10H)
1.33 (m, 6H)
0.95 (m, 15H)
$^{19}$F-NMR (282 MHz, solvent: $CDCl_3$, standard substance: $CF_3Cl$)
δ −78.76 (s, 6F)
$^{31}$P-NMR (121 MHz, solvent: $CDCl_3$, standard substance: triphenylphosphine)
δ 43.27 (m, 1P)

The structural formula is shown below (in the formula, the dashed lines show a conjugated structure).

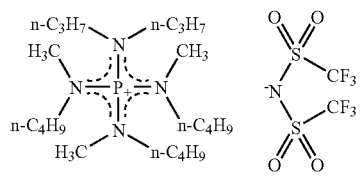

[Chemical formula 54]

The melting point was measured with a differential scanning calorimeter (DSC8230, manufactured by Shimadzu Corp.). The glass transition temperature was −71.4° C. The thermal decomposition temperature was measured with a thermal gravimetry analyzer (TG8120, manufactured by Rigaku Corp.). The 5% weight-loss temperature measured at a temperature rise rate of 10° C./min was 386.7° C.

Example 17

B(r) Preparation of tris(N-methyl-n-butylamino)di-n-butylaminophosphonium iodide In a 100 ml three-necked flask equipped with a refluxing condenser and a magnetic stirrer, 0.90 g (about 0.0025 mol) of crude tris(N-methyl-n-butylamino) phosphoimine hydrochloride obtained in B(k) was charged, and an aqueous solution dissolving 0.20 g (0.0050 mol) of NaOH in 0.5 ml of ultrapure water was slowly added dropwise. An orange-colored suspension was obtained after 1 hour stirring at room temperature. Subsequently, an aqueous solution dissolving 0.50 g (0.0125 mol) of NaOH in 2 ml of ultrapure water and 2.05 ml (0.0175 mol) of iodo-n-butane were added, and the resulting reaction mixture was stirred at 70° C. for 15.5 hours.

After the temperature was returned back to room temperature, 50 ml of $CH_2Cl_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 1.05 g of tris (N-methyl-n-butylamino)di-n-butylaminophosphonium iodide (the yield was 76% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 2.98 (m, 10H)

2.83 (d, 9H)

1.58 (m, 10H)

1.35 (m, 10H)

0.93 (t, 15H)

$^{31}$P-NMR (121 MHz, solvent: CDCl$_3$, standard substance: triphenylphosphine)

δ 43.22 (m, 1P)

The structural formula is shown below (in the formula, the dashed lines show a conjugated structure).

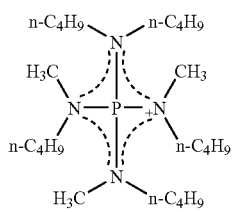

[Chemical formula 55]

B(s) Preparation of tris(N-methyl-n-butylamino)di-n-butylaminophosphonium bistrifluoromethane sulfonylimide To 1.05 g (0.0019 mol) of tris(N-methyl-n-butylamino)di-n-propylaminophosphonium iodide obtained in B(r), an aqueous solution dissolving 0.6 g (0.002 mol) of LiTFSI in 15 ml of ultrapure water was added, and the resulting solution was stirred at 50° C. for 39 hours. The resulting salt was extracted with 100 ml of CH$_2$Cl$_2$ and washed with ultrapure water three times. The extracted solution was concentrated with a rotary evaporator, vacuum-dried at 80° C. to obtain 0.41 g of tis(N-methyl-n-butylamino)di-n-butylaminophosphonium bistrifluoromethane sulfonylimide; the yield was 31%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 2.94 (m, 10H)

2.75 (d, 9H)

1.55 (m, 10H)

1.33 (m, 10H)

0.97 (t, 15H)

$^{19}$F-NMR (282 MHz, solvent: CDCl$_3$, standard substance: CF$_3$Cl)

δ −78.77 (s, 6F)

$^{31}$P-NMR (121 MHz, solvent: CDCl$_3$, standard substance: triphenylphosphine)

δ 43.44 (m, 1P)

The structural formula is shown below (in the formula, the dashed lines show a conjugated structure).

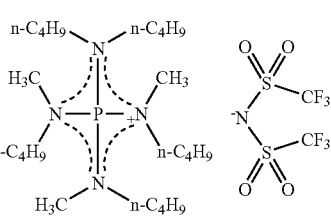

[Chemical formula 56]

The melting point was measured with a differential scanning calorimeter (DSC8230, manufactured by Shimadzu Corp.). The glass transition temperature was −70.5° C. The thermal decomposition temperature was measured with a thermal gravimetry analyzer (TG8120, manufactured by Rigaku Corp.). The 5% weight-loss temperature measured at a temperature rise rate of 10° C./min was 387.2° C.

Example 18

B(t) Preparation of tris(N-methyl-n-butylamino) dimethoxyethylaminophosphonium bromide In a 100 ml three-necked flask equipped with a refluxing condenser and a magnetic stirrer, 0.90 g (about 0.0025 mol) of crude tris(N-methyl-n-butylamino) phosphoimine hydrochloride obtained in B(k) was charged, and an aqueous solution dissolving 0.20 g (0.0050 mol) of NaOH in 0.5 ml of ultrapure water was slowly added dropwise. An orange-colored suspension was obtained after 1 hour stirring at room temperature. Subsequently, an aqueous solution dissolving 0.50 g (0.0125 mol) of NaOH in 2 ml of ultrapure water and 1.67 ml (0.0175 mol) of 2-methoxyethyl bromide were added, and the resulting reaction mixture was stirred at 70° C. for 15.5 hours.

After the temperature was returned back to room temperature, 50 ml of CH$_2$Cl$_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 0.78 g of tris (N-methyl-n-butylamino)dimethoxyethylaminophosphonium bromide (the yield was 56% based on PCl$_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.62 (t, 4H)

3.36 (s, 6H)

3.32 (m, 4H)

2.98 (m, 6H)

2.82 (d, 9H)

1.57 (m, 6H)

1.31 (m, 6H)

0.96 (t, 9H)

$^{31}$P-NMR (121 MHz, solvent: CDCl$_3$, standard substance: triphenylphosphine)

δ 44.16 (m, 1P)

The structural formula is shown below (in the formula, the dashed lines show a conjugated structure).

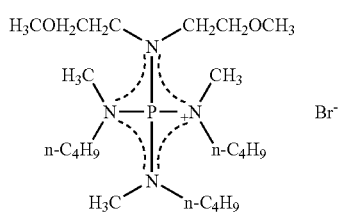

[Chemical formula 57]

B(u) Preparation of tris(N-methyl-n-butylamino) dimethoxyethylaminophosphonium bistrifluoromethane sulfonylimide To 0.78 g (0.0013 mol) of tris(N-methyl-n-butylamino) dimethoxyethylaminophosphonium bromide obtained in B(t), an aqueous solution dissolving 0.6 g (0.002 mol) of LiTFSI in 15 ml of ultrapure water was added, and the resulting solution was stirred at 50° C. for 39 hours. The resulting salt was extracted with 100 ml of $CH_2Cl_2$ and washed with ultrapure water three times. The extracted solution was concentrated with a rotary evaporator, vacuum-dried at 80° C. to obtain 0.93 g of tris(N-methyl-n-butylamino)dimethoxyethylaminophosphonium bistrifluoromethane sulfonylimide; the yield was 99%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.55 (t, 4H)
3.34 (s, 6H)
3.24 (m, 4H)
2.93 (m, 6H)
2.75 (d, 9H)
1.55 (m, 6H)
1.32 (m, 6H)
0.96 (t, 9H)
$^{19}$F-NMR (282 MHz, solvent: $CDCl_3$, standard substance: $CF_3Cl$)
δ −78.76 (s, 6F)
$^{31}$P-NMR (121 MHz, solvent: $CDCl_3$, standard substance: triphenylphosphine)
δ 44.28 (m, 1P)

The structural formula is shown below (in the formula, the dashed lines show a conjugated structure).

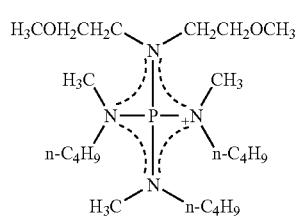

[Chemical formula 58]

The melting point was measured with a differential scanning calorimeter (DSC8230, manufactured by Shimadzu Corp.). The melting point was 20.8° C. The glass transition temperature was −68.1° C. The thermal decomposition temperature was measured with a thermal gravimetry analyzer (TG8120, manufactured by Rigaku Corp.). The 5% weight-loss temperature measured at a temperature rise rate of 10° C./min was 396.1° C.

Example 19

B(v) Preparation of tris(N-methyl-ethylamino)phosphoimine hydrochloride

In a 500 ml three-necked flask equipped with a refluxing condenser, a dropping funnel, and a magnetic stirrer, at room temperature in a nitrogen gas atmosphere, 10.0 g (0.0728 mol) of phosphorus trichloride and 92 ml (0.954 mol) of carbon tetrachloride were charged, and cooled to 5° C. or less in an ice bath. Subsequently, 37 ml (0.420 mol) of N-methylethylamine were slowly added dropwise at a temperature below 30° C. with stirring. After the temperature became constant, the resulting reaction mixture was further stirred for 1 hour at room temperature so as to obtain a yellow liquid. Then, anhydrous ammonia was bubbled from the bottom of the liquid at 25° C. for about 1.5 hours so as to obtain a faint yellow suspension. After bubbling, the suspension was further stirred overnight. The suspension was filtered off, and the resulting residue was washed with 10 ml of carbon tetrachloride. The filtrate obtained was vacuum-distilled to remove the solvent. In the form of a honey-like yellow viscous liquid were obtained 19.76 g of tris(N-methyl-ethylamino) phosphoimine hydrochloride.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 9.93 (broad, 1H)
3.11 (m, 6H)
2.75 (d, 9H)
1.20 (t, 9H)
$^{31}$P-NMR (121 MHz, solvent: $CDCl_3$, standard substance: triphenylphosphine)
δ 41.21 (m, 1P)

The structural formula is shown below.

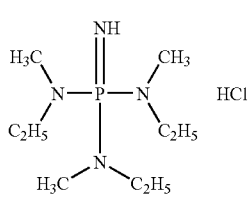

[Chemical formula 59]

B(w) Preparation of tris(N-methyl-ethylamino)dimethylaminophosphonium iodide

In a 50 ml three-necked flask equipped with a refluxing condenser and a magnetic stirrer, 3.23 g (0.0126 mol) of crude tris(N-methyl-ethylamino)phosphoimine hydrochloride obtained in B(v) were charged, and an aqueous solution dissolving 1.01 g (0.0252 mol) of NaOH in 1 ml of ultrapure water was slowly added dropwise. An orange-colored suspension was obtained after 1 hour stirring at room temperature. Subsequently, an aqueous solution dissolving 2.52 g (0.0629 mol) of NaOH in 10 ml of ultrapure water and 5.44 ml (0.0881 mol) of iodomethane were added, and the resulting reaction mixture was stirred at 70° C. for 4 hours.

After the temperature was returned back to room temperature, 50 ml of $CH_2Cl_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 3.27 g of tris(N-methyl-ethylamino)dimethylaminophosphonium iodide (the yield was 73% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.18-3.07 (m, 6H)

2.85 (d-d, 15H)

1.25 (t, 9H)

$^{31}$P-NMR (121 MHz, solvent: $CDCl_3$, standard substance: triphenylphosphine)

δ 42.69 (m, 1P)

The structural formula is shown below (in the formula, the dashed lines show a conjugated structure).

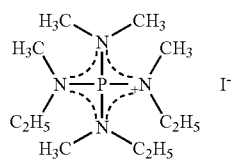

[Chemical formula 60]

B(x) Preparation of tris(N-methyl-ethylamino)dimethylaminophosphonium bistrifluoromethane sulfonylimide To 3.27 g (0.0087 mol) of tris(N-methyl-ethylamino)dimethylaminophosphonium iodide obtained in B(w), an aqueous solution dissolving 2.8 g (0.0096 mol) of LiTFSI in 100 ml of ultrapure water was added, and the resulting solution was stirred at 50° C. for 87.5 hours. The resulting salt was extracted with 100 ml of $CH_2Cl_2$ and washed with ultrapure water three times. The extracted solution was concentrated with a rotary evaporator, vacuum-dried at 80° C. to obtain 3.92 g of tis(N-methyl-ethylamino)dimethylaminophosphonium bistrifluoromethane sulfonylimide; the yield was 85%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.09-2.99 (m, 6H)

2.75 (d-d, 15H)

1.22 (t, 9H)

$^{19}$F-NMR (282 MHz, solvent: $CDCl_3$, standard substance: $CF_3Cl$)

δ −78.83 (s, 6F)

$^{31}$P-NMR (121 MHz, solvent: $CDCl_3$, standard substance: triphenylphosphine)

δ 42.86 (m, 1P)

The structural formula is shown below (in the formula, the dashed lines show a conjugated structure).

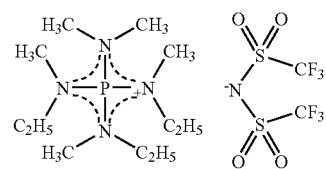

[Chemical formula 61]

The melting point was measured with a differential scanning calorimeter (DSC8230, manufactured by Shimadzu Corp.). The melting point was 127.6° C. The crystallization temperature was 123.3° C. The thermal decomposition temperature was measured with a thermal gravimetry analyzer (TG8120, manufactured by Rigaku Corp.). The 5% weight-loss temperature measured at a temperature rise rate of 10° C./min was 411.4° C.

B(y) Preparation of tris(N-methyl-ethylamino)diethylaminophosphonium iodide

In a 50 ml three-necked flask equipped with a refluxing condenser and a magnetic stirrer, 3.10 g (0.0121 mol) of crude tris(N-methyl-ethylamino)phosphoimine hydrochloride obtained in B(v) were charged, and an aqueous solution dissolving 0.96 g (0.0241 mol) of NaOH in 1 ml of ultrapure water was slowly added dropwise. An orange-colored suspension was obtained after 1 hour stirring at room temperature. Subsequently, an aqueous solution dissolving 2.42 g (0.0604 mol) of NaOH in 10 ml of ultrapure water and 6.8 ml (0.0845 mol) of iodoethane were added, and the resulting reaction mixture was stirred at 70° C. for 20 hours.

After the temperature was returned back to room temperature, 50 ml of $CH_2Cl_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 3.33 g of tris(N-methyl-ethylamino)diethylaminophosphonium iodide (the yield: 72% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.21-3.08 (m, 10H)

2.84 (d, 9H)

1.25 (t, 15H)

$^{31}$P-NMR (121 MHz, solvent: $CDCl_3$, standard substance: triphenylphosphine)

δ 43.02 (m, 1P)

The structural formula is shown below (in the formula, the dashed lines show a conjugated structure).

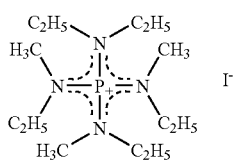

[Chemical formula 62]

B(z) Preparation of tris(N-methyl-ethylamino)diethylaminophosphonium bistrifluoromethane sulfonylimide To 3.33 g (0.00824 mol) of tris(N-methyl-ethylamino)diethylaminophosphonium iodide obtained in B(y), an aqueous solution dissolving 2.6 g (0.0091 mol) of LiTFSI in 100 ml of ultrapure water was added, and the resulting solution was stirred at 50° C. for 87.5 hours. The resulting salt was extracted with 100 ml of $CH_2Cl_2$ and washed with ultrapure water three times. The extracted solution was concentrated with a rotary evaporator, vacuum-dried at 80° C. to obtain 3.77 g of tis(N-methyl-ethylamino) diethylaminophosphonium bistrifluoromethane sulfonylimide; the yield was 82%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.17-2.99 (m, 10H)
2.75 (d, 9H)
1.22 (t, 15H)

$^{19}$F-NMR (282 MHz, solvent: $CDCl_3$, standard substance: $CF_3Cl$)
δ −78.85 (s, 6F)

$^{31}$P-NMR (121 MHz, solvent: $CDCl_3$, standard substance: triphenylphosphine)
δ 43.11 (m, 1P)

The structural formula is shown below (in the formula, the dashed lines show a conjugated structure).

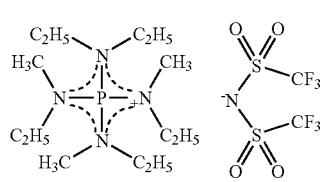

[Chemical formula 63]

The melting point was measured with a differential scanning calorimeter (DSC8230, manufactured by Shimadzu Corp.). The melting point was 115.7° C. The thermal decomposition temperature was measured with a thermal gravimetry analyzer (TG8120, manufactured by Rigaku Corp.). The 5% weight-loss temperature measured at a temperature rise rate of 10° C./min was 408.7° C.

B(aa) Preparation of tris(N-methyl-ethylamino)di-n-propylaminophosphonium iodide In a 50 ml three-necked flask equipped with a refluxing condenser and a magnetic stirrer, 2.00 g (0.00779 mol) of crude tris(N-methyl-ethylamino)phosphoimine hydrochloride obtained in B(v) were charged, and an aqueous solution dissolving 0.62 g (0.00156 mol) of NaOH in 1 ml of ultrapure water was slowly added dropwise. An orange-colored suspension was obtained after 1 hour stirring at room temperature. Subsequently, an aqueous solution dissolving 1.56 g (0.0389 mol) of NaOH in 6 ml of ultrapure water and 5.3 ml (0.055 mol) of iodo-n-propane were added, and the resulting reaction mixture was stirred at 70° C. for 15 hours.

After the temperature was returned back to room temperature, 50 ml of $CH_2Cl_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 2.47 g of tris(N-methyl-ethylamino)di-n-propylaminophosphonium iodide (the yield: 78% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)
δ 3.18-3.08 (m, 6H)
3.02-2.92 (m, 4H)
2.83 (d, 9H)
1.67-1.59 (m, 4H)
1.25 (t, 9H)
0.96 (t, 6H)

$^{31}$P-NMR (121 MHz, solvent: $CDCl_3$, standard substance: triphenylphosphine)
δ 42.91 (m, 1P)

The structural formula is shown below (in the formula, the dashed lines show a conjugated structure).

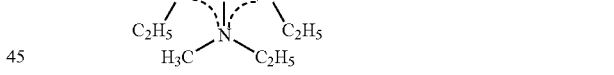

[Chemical formula 61]

B(ab) Preparation of tris(N-methyl-ethylamino)di-n-propylaminophosphonium bistrifluoromethane sulfonylimide To 2.47 g (0.00571 mol) of tris(N-methyl-ethylamino)di-n-propylaminophosphonium iodide obtained in B(aa), an aqueous solution dissolving 1.8 g (0.0063 mol) of LiTFSI in 100 ml of ultrapure water was added, and the resulting solution was stirred at 50° C. for 18 hours. The resulting salt was extracted with 100 ml of $CH_2Cl_2$ and washed with ultrapure water three times. The extracted solution was concentrated with a rotary evaporator, vacuum-dried at 80° C. to obtain 2.53 g of tis(N-methyl-ethylamino)di-n-propylaminophosphonium bistrifluoromethane sulfonylimide; the yield was 76%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.10-2.99 (m, 6H)
2.97-2.89 (m, 4H)
2.74 (d, 9H)
1.64-1.56 (m, 4H)
1.22 (t, 9H)
0.93 (t, 6H)

$^{19}$F-NMR (282 MHz, solvent: CDCl$_3$, standard substance: CF$_3$Cl)

δ −78.88 (s, 6F)

$^{31}$P-NMR (121 MHz, solvent: CDCl$_3$, standard substance: triphenylphosphine)

δ 42.97 (m, 1P)

The structural formula is shown below (in the formula, the dashed lines show a conjugated structure).

[Chemical formula 65]

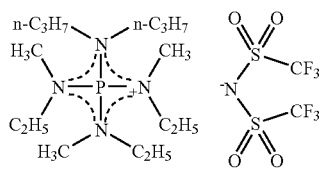

The melting point was measured with a differential scanning calorimeter (DSC8230, manufactured by Shimadzu Corp.). No peak, which can be recognized as a melting point, was observed. The thermal decomposition temperature was measured with a thermal gravimetry analyzer (TG8120, manufactured by Rigaku Corp.). The 5% weight-loss temperature measured at a temperature rise rate of 10° C./min was 402.8° C.

B(ac) Preparation of tris(N-methyl-ethylamino)di-n-butylaminophosphonium iodide

In a 50 ml three-necked flask equipped with a refluxing condenser and a magnetic stirrer, 2.06 g (0.00802 mol) of crude tris(N-methyl-ethylamino)phosphoimine hydrochloride obtained in B(v) was charged, and an aqueous solution dissolving 0.64 g (0.0160 mol) of NaOH in 1 ml of ultrapure water was slowly added dropwise. An orange-colored suspension was obtained after 1 hour stirring at room temperature. Subsequently, an aqueous solution dissolving 1.60 g (0.0401 mol) of NaOH in 6 ml of ultrapure water and 6.5 ml (0.056 mol) of iodo-n-butane were added, and the resulting reaction mixture was stirred at 70° C. for 15 hours.

After the temperature was returned back to room temperature, 50 ml of CH$_2$Cl$_2$ were added to extract the reaction mixture. The separated organic layer was washed with ultrapure water five times, vacuum-distilled to remove most of the solvent, vacuum-dried at 80° C., further washed with ether three times, vacuum-distilled again to remove most of the solvent, and vacuum-dried at 80° C. to obtain 2.72 g of tris(N-methyl-ethylamino)di-n-butylaminophosphonium iodide (the yield: 78% based on PCl$_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.19-3.08 (m, 6H)
3.05-2.96 (m, 4H)
2.83 (d, 9H)
1.56 (m, 4H)
1.39-1.31 (m, 4H)
1.25 (t, 9H)
0.97 (t, 6H)

$^{31}$P-NMR (121 MHz, solvent: CDCl$_3$, standard substance: triphenylphosphine)

δ 43.02 (m, 1P)

The structural formula is shown below (in the formula, the dashed lines show a conjugated structure).

[Chemical formula 66]

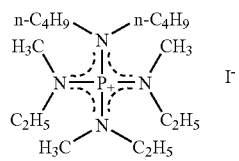

B(ad) Preparation of tris(N-methyl-ethylamino)di-n-butylaminophosphonium bistrifluoromethane sulfonylimide To 2.72 g (0.00590 mol) of tris(N-methyl-ethylamino)di-n-butylaminophosphonium iodide obtained in B(ac), an aqueous solution dissolving 1.9 g (0.0066 mol) of LiTFSI in 100 ml of ultrapure water was added, and the resulting solution was stirred at 50° C. for 18 hours. The resulting salt was extracted with 100 ml of CH$_2$Cl$_2$ and washed with ultrapure water three times. The extracted solution was concentrated with a rotary evaporator, vacuum-dried at 80° C. to obtain 2.56 g of tris(N-methyl-ethylamino)di-n-butylaminophosphonium bistrifluoromethane sulfonylimide; the yield was 71%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.10-2.91 (m, 10H)
2.74 (d, 9H)
1.55 (m, 4H)
1.36-1.29 (m, 4H)
1.21 (t, 9H)
0.96 (t, 6H)

$^{19}$F-NMR (282 MHz, solvent: CDCl$_3$, standard substance: CF$_3$Cl)

δ −78.86 (s, 6F)

$^{31}$P-NMR (121 MHz, solvent: CDCl$_3$, standard substance: triphenylphosphine)

δ 43.06 (m, 1P)

The structural formula is shown below (in the formula, the dashed lines show a conjugated structure).

[Chemical formula 67]

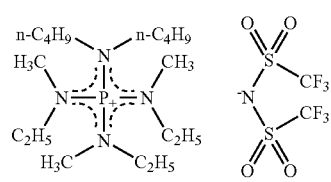

The melting point was measured with a differential scanning calorimeter (DSC8230, manufactured by Shimadzu Corp.). The melting point was −20.8° C. The glass transition temperature was −83.7° C. The thermal decomposition temperature was measured with a thermal gravimetry analyzer (TG8120, manufactured by Rigaku Corp.). The 5% weight-loss temperature measured at a temperature rise rate of 10° C./min was 406.0° C.

B(ae) Preparation of tris(N-methyl-ethylamino)di-n-butylaminophosphonium trifluoroborate To 1.00 g (0.00217 mol) of tris(N-methyl-ethylamino)di-n-butylaminophosphonium iodide obtained in B(ac), an aqueous solution dissolving 0.3 g (0.0026 mol) of $NaBF_4$ in 2 ml of a 1 wt. % NaOH aqueous solution was added, and the resulting solution was stirred at 60° C. for 2 hours. After the resulting water layer was removed, the reaction mixture was washed with 2 ml of a 1 wt. % NaOH aqueous solution and 2 ml of ultrapure water, and then vacuum-dried at 80° C. to obtain 0.23 g of tris(N-methyl-ethylamino)di-n-butylaminophosphonium trifluoroborate; the yield was 25%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.08 (m, 6H)
2.98 (m, 4H)
2.78 (d, 9H)
1.56 (m, 4H)
1.34 (m, 4H)
1.23 (t, 9H)
0.96 (t, 6H)

$^{19}$F-NMR (282 MHz, solvent: $CDCl_3$, standard substance: $CF_3Cl$)

δ −153.52 (d, 4F)

$^{31}$P-NMR (121 MHz, solvent: $CDCl_3$, standard substance: triphenylphosphine)

δ 43.24 (m, 1P)

The structural formula is shown below (in the formula, the dashed lines shows a conjugated structure).

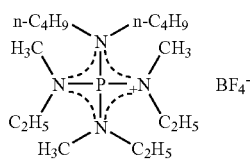

[Chemical formula 68]

The melting point was measured with a differential scanning calorimeter (DSC8230, manufactured by Shimadzu Corp.). The glass transition temperature was −61.6° C. The thermal decomposition temperature was measured with a thermal gravimetry analyzer (TG8120, manufactured by Rigaku Corp.). The 5% weight-loss temperature measured at a temperature rise rate of 10° C./min was 309.2° C.

B(af) Preparation of tris(N-methyl-ethylamino)di-n-butylaminophosphonium hexafluorophosphate To 1.00 g (0.00217 mol) of tris(N-methyl-ethylamino)di-n-butylaminophosphonium iodide obtained in B(ac), an aqueous solution dissolving 0.40 g (0.0026 mol) of $LiPF_6$ in 5 ml of ultrapure water was added, and the resulting solution was stirred at room temperature for 20 hours. The resulting salt was extracted with 10 ml of $CH_2Cl_2$ and washed with ultrapure water three times. The extracted solution was concentrated with a rotary evaporator, and vacuum-dried at 80° C. so as to obtain 0.97 g of tris(N-methyl-ethylamino)di-n-butylaminophosphonium hexafluorophosphate; the yield was 93%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.05 (m, 6H)
2.97 (m, 4H)
2.75 (d, 9H)
1.55 (m, 4H)
1.33 (m, 4H)
1.22 (t, 9H)
0.96 (t, 6H)

$^{19}$F-NMR (282 MHz, solvent: $CDCl_3$, standard substance: $CF_3Cl$)

δ −73.27 (d, 6F)

$^{31}$P-NMR (121 MHz, solvent: $CDCl_3$, standard substance: triphenylphosphine)

δ 43.26 (m, 1P)
−144.30 (hept, 1P)

The structural formula is shown below (in the formula, the dashed lines shows a conjugated structure).

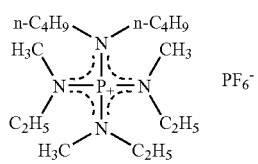

[Chemical formula 69]

The melting point was measured with a differential scanning calorimeter (DSC8230, manufactured by Shimadzu Corp.). The glass transition temperature was −61.7° C. The thermal decomposition temperature was measured with a thermal gravimetry analyzer (TG8120, manufactured by Rigaku Corp.). The 5% weight-loss temperature measured at a temperature rise rate of 10° C./min was 296.5° C.

B(ag) Preparation of tris(N-methyl-ethylamino)di-n-butylaminophosphonium dicyanamide In 5 ml of ultrapure water was dissolved 0.46 g (0.0010 mol) of tris(N-methyl-ethylamino)di-n-butylaminophosphonium iodide obtained in B(ac), and 0.21 g (0.0012 mol) of $AgN(CN)_2$ that was prepared from silver nitrate and $NaN(CN)_2$ was added. Then, the resulting reaction mixture was stirred at room temperature for 20 hours. After 10 ml of dichloromethane were added to the reaction mixture, and the reaction mixture was stirred for a while, the resulting crystals were filtered off so as to separate the resulting water layer. Through washing three times with ultrapure water, vacuum-concentration with a rotary evaporator, and vacuum drying at 80° C., 0.27 g of tris(N-methyl-ethylamino)di-n-butylaminophosphonium dicyanamide was obtained; the yield was 68%.

The resulting compound was identified with a nuclear magnetic resonance analyzer (BRUKER Ultra Shield 300

NMR Spectrometer, manufactured by BRUKER Limited). The resulting spectral data are shown below.

$^1$H-NMR (300 MHz, solvent: CDCl$_3$, standard substance: tetramethylsilane)

δ 3.15-2.96 (m, 10H)
2.80 (d, 9H)
1.58 (m, 4H)
1.36 (m, 4H)
1.23 (t, 9H)
0.98 (t, 6H)

$^{31}$P-NMR (121 MHz, solvent: CDCl$_3$, standard substance: triphenylphosphine)

δ 43.17 (m, 1P)

The structural formula is shown below (in the formula, the dashed lines shows a conjugated structure).

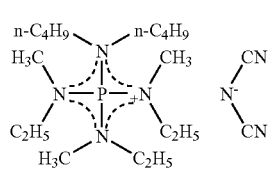

[Chemical formula 70]

The melting point was measured with a differential scanning calorimeter (DSC8230, manufactured by Shimadzu Corp.). The glass transition temperature was −66.8° C. The thermal decomposition temperature was measured with a thermal gravimetry analyzer (TG8120, manufactured by Rigaku Corp.). The 5% weight-loss temperature measured at a temperature rise rate of 10° C./min was 270.8° C.

B(ah) Preparation of tris(N-methyl-ethylamino)di-n-pentylaminophosphonium iodide In a 50 ml three-necked flask equipped with a refluxing condenser and a magnetic stirrer, 1.01 g (about 0.0039 mol) of crude tris(N-methyl-ethylamino)phosphoimine hydrochloride obtained in B(v) were charged, and an aqueous solution dissolving 0.314 g (0.00787 mol) of NaOH in 0.5 ml of ultrapure water was slowly added dropwise. An orange-colored suspension was obtained after 1 hour stirring at room temperature. Subsequently, an aqueous solution dissolving 0.79 g (0.0197 mol) of NaOH in 3 ml of ultrapure water and 3.1 ml (0.028 mol) of iodopentane were added, and the resulting reaction mixture was stirred at 70° C. for 6 hours.

After the temperature was returned back to room temperature, 50 ml of CH$_2$Cl$_2$ were added to extract the reaction mixture. The separated organic layer was washed with ultrapure water three times, vacuum-distilled to remove most of the solvent, and vacuum-dried at 80° C. to obtain 1.58 g of tris(N-methyl-ethylamino)di-n-pentylaminophosphonium iodide (the yield: 82% based on PCl$_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.12 (m, 6H)
2.99 (m, 4H)
2.82 (d, 9H)
1.57 (m, 4H)
1.42-1.23 (m, 17H)
0.92 (t, 6H)

$^{31}$P-NMR (121 MHz, solvent: CDCl$_3$, standard substance: triphenylphosphine)

δ 43.00 (m, 1P)

The structural formula is shown below (in the formula, the dashed lines show a conjugated structure).

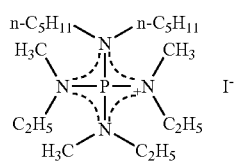

[Chemical formula 71]

B(ai) Preparation of tris(N-methyl-ethylamino)di-n-pentylaminophosphonium bistrifluoromethane sulfonylimide To 0.95 g (0.0019 mol) of tris(N-methyl-ethylamino)di-n-pentylaminophosphonium iodide obtained in B(ah), an aqueous solution dissolving 0.9 g (0.0021 mol) of LiTFSI in 5 ml of ultrapure water was added, and the resulting solution was stirred at room temperature for 18 hours. The resulting salt was extracted with 10 ml of CH$_2$Cl$_2$ and washed with ultrapure water three times. The extracted solution was concentrated with a rotary evaporator, vacuum-dried at 80° C. to obtain 0.94 g of tris(N-methyl-ethylamino)di-n-pentylaminophosphonium bistrifluoromethane sulfonylimide; the yield was 75%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.10-2.94 (m, 10H)
2.79 (d, 9H)
1.56 (m, 4H)
1.40-1.19 (m, 17H)
0.92 (t, 6H)

$^{19}$F-NMR (282 MHz, solvent: CDCl$_3$, standard substance: CF$_3$Cl)

δ −78.81

$^{31}$P-NMR (121 MHz, solvent: CDCl$_3$, standard substance: triphenylphosphine)

δ 43.18 (m, 1P)

The structural formula is shown below (in the formula, the dashed lines show a conjugated structure).

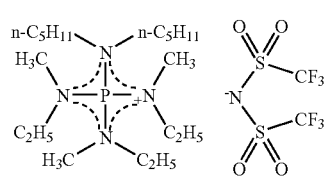

[Chemical formula 72]

The melting point was measured with a differential scanning calorimeter (DSC8230, manufactured by Shimadzu Corp.). The glass transition temperature was −78.8° C. The thermal decomposition temperature was measured with a thermal gravimetry analyzer (TG8120, manufactured by Rigaku Corp.). The 5% weight-loss temperature measured at a temperature rise rate of 10° C./min was 366.5° C.

B(aj) Preparation of tris(N-methyl-ethylamino) dimethoxyethylaminophosphonium bromide In a 50 ml three-necked flask equipped with a refluxing condenser and a magnetic stirrer, 2.06 g (0.0082 mol) of crude tris(N-methyl-ethylamino)phosphoimine hydrochloride obtained in B(v) were charged, and an aqueous solution dissolving 0.64 g (0.016 mol) of NaOH in 1 ml of ultrapure water was slowly added dropwise. An orange-colored suspension was obtained after 1 hour stirring at room temperature. Subsequently, an aqueous solution dissolving 1.60 g (0.0401 mol) of NaOH in 5 ml of ultrapure water and 5.3 ml (0.058 mol) of 2-methoxyethyl bromide were added, and the resulting reaction mixture was stirred at 70° C. for 18 hours.

After the temperature was returned back to room temperature, 50 ml of $CH_2Cl_2$ were added to extract the reaction mixture. The separated organic layer was washed with ultrapure water three times, vacuum-distilled to remove most of the solvent, washed with ether three times, and vacuum-dried at 80° C. to obtain 1.97 g of tris(N-methyl-ethylamino) dimethoxyethylaminophosphonium bromide (the yield: 62% based on $PCl_3$).

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.60 (t, 4H)
3.36-3.30 (m, 10H)
3.15-3.10 (m, 6H)
2.81 (d, 9H)
1.22 (t, 9H)

$^{31}$P-NMR (121 MHz, solvent: $CDCl_3$, standard substance: triphenylphosphine)

δ 43.99 (m, 1P)

The structural formula is shown below (in the formula, the dashed lines show a conjugated structure).

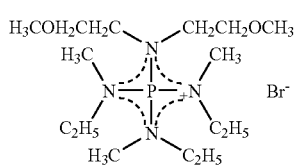

[Chemical formula 73]

B(ak) Preparation of tris(N-methyl-ethylamino) dimethoxyethylaminophosphonium bistrifluoromethane sulfonylimide To 1.97 g (0.00472 mol) of tris(N-methyl-ethylamino)dimethoxyethylaminophosphonium bromide obtained in B(aj), an aqueous solution dissolving 1.5 g (0.0052 mol) of LiTFSI in 50 ml of ultrapure water was added, and the resulting solution was stirred at 50° C. for 64 hours. The resulting salt was extracted with 100 ml of $CH_2Cl_2$ and washed with ultrapure water three times. The extracted solution was concentrated with a rotary evaporator, vacuum-dried at 80° C. to obtain 1.36 g of tris(N-methyl-ethylamino)dimethoxyethylaminophosphonium bistrifluoromethane sulfonylimide; the yield was 47%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: $CDCl_3$, standard substance: tetramethylsilane)

δ 3.54 (t, J=4.8 Hz, 4H)
3.34 (s, 6H)
3.28-3.21 (m, 4H)
3.11-3.01 (m, 6H)
2.74 (d, 9H)
1.20 (t, 9H)

$^{19}$F-NMR (282 MHz, solvent: $CDCl_3$, standard substance: $CF_3Cl$)

δ -78.86 (s, 6F)

$^{31}$P-NMR (121 MHz, solvent: $CDCl_3$, standard substance: triphenylphosphine)

δ 44.06 (m, 1P)

The structural formula is shown below (in the formula, the dashed lines show a conjugated structure).

[Chemical formula 74]

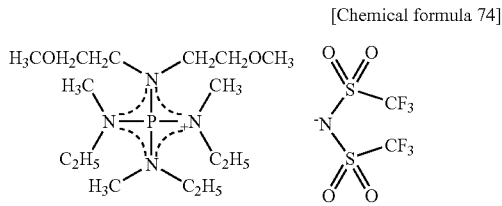

The melting point was measured with a differential scanning calorimeter (DSC8230, manufactured by Shimadzu Corp.). The glass transition temperature was -76.7° C. The thermal decomposition temperature was measured with a thermal gravimetry analyzer (TG8120, manufactured by Rigaku Corp.). The 5% weight-loss temperature measured at a temperature rise rate of 10° C./min was 382.9° C.

B(am) Preparation of bis(N,N'-dimethylethylenediamino)phosphonium bistrifluoromethane sulfonylimide In a nitrogen gas stream, 3.00 g (19.7 mmol) of chloro(N, N'-dimethylethylenediamino)phosphine obtained in (m) and 50 ml of $CCl_4$ dried with $CaCl_2$ were charged. At 0° C., 2.12 ml (19.7 mmol) of N,N'-dimethylethylenediamine and 2.75 ml (19.7 mmol) of triethylamine were successively added dropwise. The resulting reaction mixture was stirred at room temperature for 20 hours. Subsequently, the reaction mixture was dissolved in $CH_2Cl_2$, and the resulting solution was filtered so as to remove crystals. Through concentration with a rotary evaporator, 4.01 g of a brown viscous solid were obtained. After the solid was dissolved in water and washed with $CH_2Cl_2$ to remove impurities, to the resulting aqueous solution was added an aqueous solution dissolving 5.7 g (19.7 mmol) of LiTFSI in 10 ml of ultrapure water. The resulting solution was stirred at room temperature for four days, and then extracted with 30 ml of $CH_2Cl_2$ twice. The resulting organic phase was washed with 50 ml of ultrapure water three times. Through concentration with a rotary evaporator, washing three times with diethyl ether, vacuum drying, and recrystallization with $CH_2Cl_2/Et_2O$, 0.79 g of bis(N,N'-dimethylethylenediamino) phosphonium bistrifluoromethane sulfonylimide was obtained in the form of a white solid; the yield was 8%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.41 (d, 8H)

2.68 (d, 12H)

$^{19}$F-NMR (282 MHz, solvent: CDCl$_3$, standard substance: CF$_3$Cl)

δ −78.87 (s, 6F)

$^{31}$P-NMR (121 MHz, solvent: CDCl$_3$, standard substance: triphenylphosphine)

δ 43.58 (m, 1P)

The structural formula is shown below (in the formula, the dashed lines show a conjugated structure).

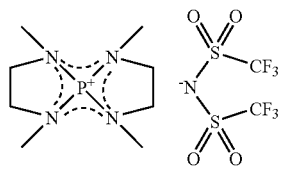

[Chemical formula 75]

The melting point was measured with a differential scanning calorimeter (DSC8230, manufactured by Shimadzu Corp.). The melting point was 153.4° C. The crystallization temperature was 133.95° C. The thermal decomposition temperature was measured with a thermal gravimetry analyzer (TG8120, manufactured by Rigaku Corp.). The 5% weight-loss temperature measured at a temperature rise rate of 10° C./min was 403.8° C.

B(an) Preparation of tris(N-methyl-ethylamino)di-n-pentylaminophosphonium heptafluorobutyrate In 50 ml of ultrapure water, 0.48 g (0.0010 mol) of tris(N-methyl-ethylamino)di-n-pentylaminophosphonium iodide obtained in B(ah) was dissolved, and 0.32 g (0.0010 mol) of silver heptafluorobutyrate was added. The resulting reaction mixture was stirred at room temperature for 1 hour. After the solvent was distilled out with a rotary evaporator, 30 ml of chloroform were added and the resulting solid was precipitated with a centrifugal separator so as to take out a supernatant solution. Through vacuum-concentration with a rotary evaporator, washing three times with 2 ml of ultrapure, and vacuum drying at 50° C. was obtained 0.49 g of tris(N-methyl-ethylamino)di-n-pentylaminophosphonium heptafluorobutyrate; the yield was 87%.

The resulting compound was identified with a nuclear magnetic resonance analyzer (BRUKER Ultra Shield 300 NMR Spectrometer, manufactured by BRUKER Limited). The resulting spectral data are shown below.

$^1$H-NMR (300 MHz, solvent: CDCl$_3$, standard substance: tetramethylsilane)

δ 3.07 (m, 6H)

2.96 (m, 4H)

2.77 (d, 9H)

1.56 (m, 4H)

1.39-1.20 (m, 17H)

0.92 (t, 6H)

$^{19}$F-NMR (282 MHz, solvent: CDCl$_3$, standard substance: CF$_3$Cl)

δ −80.71 (t, 3F)

−116.58 (q, 2F)

−126.52 (s, 2F)

$^{31}$P-NMR (121 MHz, solvent: CDCl$_3$, standard substance: triphenylphosphine)

δ 43.18 (m, 1P)

The structural formula is shown below (in the formula, the dashed lines show a conjugated structure).

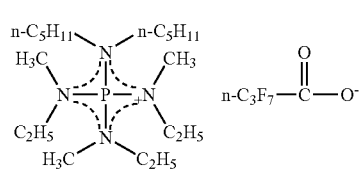

[Chemical formula 76]

The melting point was measured with a differential scanning calorimeter (DSC8230, manufactured by Shimadzu Corp.). The glass transition temperature was −72.9° C. The thermal decomposition temperature was measured with a thermal gravimetry analyzer (TG8120, manufactured by Rigaku Corp.). The 5% weight-loss temperature measured at a temperature rise rate of 10° C./min was 146.2° C.

As mentioned above, these results show that the salts of the Examples are stably in a liquid state over a wide temperature range from −20° C. to about 400° C.

INDUSTRIAL APPLICABILITY

The present invention provides an ionic liquid that is stably in a liquid state over a wide temperature range and is excellent in electrochemical stability.

The ionic liquid of the present invention can be used for applications such as lithium secondary batteries, electrical double layer capacitors, fuel cells, dye-sensitized solar cells, electrolytes, electrolyte solutions or additives of electric power storage devices, solvents for reaction or separation and extraction, sensors, electrolytic plating, polymers, plasticizers, lubricating oils, and actuators.

The invention claimed is:

1. An ionic liquid comprising a cation component and an anion component,
   (i) the cation component being one or more component selected from the group of phosphonium ion components represented by general formula (1),

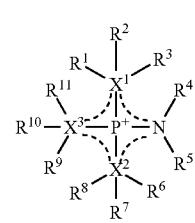

(1)

wherein,
substituents $R^1$ to $R^{11}$ are independent of each other and may be the same or different from each other, and each represent any of: a hydrogen atom, a $C_1$ to $C_{30}$ linear or branched alkyl group, a $C_2$ to $C_{30}$ linear or branched alkenyl group that has a single or plural double bond(s), a $C_2$ to $C_{30}$ linear or branched alkynyl group that has a single or plural triple bond(s), a saturated or partly or fully unsaturated cycloalkyl group, an aryl group, and a heterocyclic group;

a hydrogen atom contained in the substituent(s) $R^1$ to $R^{11}$ may be partly or fully replaced by a halogen atom or partly replaced by a CN group or a $NO_2$ group;

any substituent among the substituents $R^1$ to $R^{11}$ may form a ring structure jointly with each other;

a carbon atom contained in the substituents $R^1$ to $R^{11}$ may be replaced by an atom and/or a group of atoms selected from the group consisting of: —O—, —Si(R')$_2$—, —C(O)—, —C(O)O—, —S—, —S(O)—, —SO$_2$—, —SO$_3$—, —N=, —N=N—, —NH—, —NR'—, —PR'—, —P(O)R'—, —P(O)R'—O—, —O—P(O)R'—O—, and —P(R')$_2$=N—, wherein R' is a $C_1$ to $C_{10}$ linear or branched alkyl group, an alkyl group that is partly or fully substituted with a fluorine atom, a saturated or partly or fully unsaturated cycloalkyl group, a non-substituted or substituted phenyl group, or a non-substituted or substituted heterocycle;

$X^1$, $X^2$, and $X^3$ are independent of each other and represent a nitrogen atom, an oxygen atom, a sulfur atom, or a carbon atom, wherein the phosphonium ion of formula (1) has 1, 2 or 4 P—N bonds;

$R^3$, $R^8$, or $R^{11}$ is a substituent that exists in the formula (1) only when $X^1$, $X^2$, or $X^3$ is a carbon atom;

$X^1$, $R^1$, $R^2$, and $R^3$ may form jointly with each other a saturated or partly or fully unsaturated ring structure when $X^1$ is a carbon atom, $X^2$, $R^6$, $R^7$, and $R^8$ may form jointly with each other a saturated or partly or fully unsaturated ring structure when $X^2$ is a carbon atom, and $X^3$, $R^9$, $R^{10}$, and $R^{11}$ may form jointly with each other a saturated or partly or fully unsaturated ring structure when $X^3$ is a carbon atom;

$R^2$, $R^7$, or $R^{10}$ is a substituent that exists in the formula 1(1) only when $X^1$, $X^2$, or $X^3$ is a nitrogen atom or a carbon atom;

$X^1$, $R^1$, and $R^2$ may form jointly with each other a saturated or partly or fully unsaturated ring structure when $X^1$ is a nitrogen atom or a carbon atom, $X^2$, $R^6$, and $R^7$ may form jointly with each other a saturated or partly or fully unsaturated ring structure when $X^2$ is a nitrogen atom or a carbon atom, and $X^3$, $R^9$, and $R^{10}$ may form jointly with each other a saturated or partly or fully unsaturated ring structure when $X^3$ is a nitrogen atom or a carbon atom; and dashed lines show a conjugated structure;

(ii) the anion component being one or more component selected from the group consisting of: [(RfSO$_2$)$_2$N]$^-$, RfCOO$^-$, (RfBF$_3$)$^-$, [B(OR)$_4$]$^-$, [N(CN)$_2$]$^-$, (AlCl$_4$)$^-$, SO$_4^{2-}$, and NO$_3^-$, wherein, the substituent R represents any of a hydrogen atom, a halogen atom, a $C_1$ to $C_{10}$ linear or branched alkyl group, a $C_2$ to $C_{10}$ linear or branched alkenyl group that has a single or plural double bond(s), a $C_2$ to $C_{10}$ linear or branched alkynyl group that has a single or plural triple bond(s) and a saturated or partly or fully unsaturated cycloalkyl group;

a hydrogen atom contained in the substituent R may be partly or fully replaced by a halogen atom or partly replaced by a CN group or a $NO_2$ group;

a carbon atom contained in the substituent R may be replaced by an atom and/or a group of atoms selected from the group consisting of: —O—, —C(O)—, —C(O)O—, —S—, —S(O)—, —SO$_2$—, —SO$_3$—, —N=, —N=N—, —NR'—, —N(R')$_2$—, —PR'—, —P(O)R'—, —P(O)R'—O—, —O—P(O)R'—O—, and —P(R')$_2$=N—, wherein R' is a $C_1$ to $C_{10}$ linear or branched alkyl group, an alkyl group that is partly or fully substituted with a fluorine atom, a saturated or partly or fully unsaturated cycloalkyl group, a non-substituted or substituted phenyl group, or a non-substituted or substituted heterocycle; and Rf is a fluorine-containing substituent.

2. The ionic liquid according to claim 1, wherein the substituents $R^1$ to $R^{11}$ in the general formula (1) are a $C_1$ to $C_{30}$ linear or branched alkyl group, a saturated or partly or fully unsaturated cycloalkyl group, an aryl group, or a heterocyclic group;

a hydrogen atom contained in the single or plural substituent(s) $R^1$ to $R^{11}$ may be partly or fully replaced by a halogen atom or partly replaced by a CN group or a $NO_2$ group; and a carbon atom contained in the substituents $R^1$ to $R^{11}$ may be replaced by an atom and/or a group of atoms selected from the group consisting of —O—, —Si(R')$_2$—, —C(O)—, —C(O)O—, —S—, —S(O)—, and —NR'—, wherein R' is a $C_1$ to $C_{10}$ linear or branched alkyl group, an alkyl group that is partly or fully substituted with a fluorine atom, a saturated or partly or fully unsaturated cycloalkyl group, a non-substituted or substituted phenyl group, or a non-substituted or substituted heterocycle.

3. The ionic liquid according to claim 1, wherein $R^1$ to $R^{11}$ in the general formula (1) each are the same or different from each other, and are a $C_1$ to $C_{20}$ linear or branched alkyl or alkoxy group.

4. The ionic liquid according to claim 1, wherein the cation in the general formula (1) is of low symmetry.

5. The ionic liquid according to claim 4, wherein at least one of $R^1$ to $R^{11}$ in the general formula (1) is a different group from the others.

6. The ionic liquid according to claim 5, wherein at least one of $R^1$ to $R^{11}$ in the general formula (1) is a $C_4$ to $C_{20}$ linear or branched alkyl or alkoxy group, and the rest of R"s are a hydrogen atom or a $C_1$ to $C_4$ linear or branched alkyl group.

7. The ionic liquid according to claim 5, wherein at least one of $R^1$ to $R^{11}$ in the formula (1) has a silyl group.

8. The ionic liquid according to claim 5, wherein any of $R^1$ to $R^{11}$ in the formula (1) forms a ring structure jointly with each other.

9. The ionic liquid according to claim 1, wherein $R^1$ to $R^{11}$ in the general formula (1) are the same or different from each other, and are a $C_1$ to $C_{10}$ linear or branched alkyl or alkoxy group.

10. The ionic liquid according to claim 1, wherein at least one of $R^1$ to $R^{11}$ in the general formula (1) is a $C_4$ to $C_{20}$ linear or branched alkyl or alkoxy group, and the rest of R"s are a hydrogen atom or a $C_1$ to $C_4$ linear or branched alkyl group; and the anion component is any of (CF$_3$SO$_2$)$_2$N$^-$, PF$_6^-$, and BF$_4^-$.

11. The ionic liquid according to claim 1, wherein at least one of $R^1$ to $R^{11}$ in the general formula (1) has a silyl group.

12. The ionic liquid according to claim 1, wherein any of $R^1$ to $R^{11}$ in the formula (1) forms a ring structure jointly with each other.

* * * * *